(12) United States Patent
Lowe et al.

(10) Patent No.: US 9,415,088 B2
(45) Date of Patent: Aug. 16, 2016

(54) USE OF AGR3 FOR TREATING CANCER

(75) Inventors: Anson W. Lowe, Stanford, CA (US); Aiwen Dong, Stanford, CA (US)

(73) Assignee: The Board of Trustees of the Leland Stanford Junior University, Stanford, CT (US)

( * ) Notice: Subject to any disclaimer, the term of this patent is extended or adjusted under 35 U.S.C. 154(b) by 0 days.

(21) Appl. No.: 14/000,182

(22) PCT Filed: Feb. 27, 2012

(86) PCT No.: PCT/US2012/026682
§ 371 (c)(1),
(2), (4) Date: Oct. 24, 2013

(87) PCT Pub. No.: WO2012/116357
PCT Pub. Date: Aug. 30, 2012

(65) Prior Publication Data
US 2014/0050781 A1    Feb. 20, 2014

Related U.S. Application Data

(60) Provisional application No. 61/446,916, filed on Feb. 25, 2011.

(51) Int. Cl.
*A61K 38/17* (2006.01)
*A61K 45/06* (2006.01)

(52) U.S. Cl.
CPC ............. *A61K 38/1709* (2013.01); *A61K 45/06* (2013.01)

(58) Field of Classification Search
CPC .............. A61K 38/1709; A61K 45/06; A61K 38/1761; A61K 38/1764; A61K 48/005; A61K 48/0058; A61K 31/7088; A61K 2039/53; A61K 48/00; C12Q 2600/178
See application file for complete search history.

(56) References Cited

U.S. PATENT DOCUMENTS

| 6,171,816 B1 * | 1/2001 | Yu et al. ........................ 435/69.1 |
| 7,601,505 B2 | 10/2009 | Monahan et al. |
| 2007/0231822 A1 | 10/2007 | Mitas |

FOREIGN PATENT DOCUMENTS

| WO | WO2004031239 A2 | 4/2004 |
| WO | WO2004056858 A2 | 7/2004 |
| WO | WO2006061414 A1 | 6/2006 |
| WO | WO2006061418 A2 | 6/2006 |
| WO | WO2008025964 A2 | 3/2008 |
| WO | WO2012116357 A2 | 8/2012 |

OTHER PUBLICATIONS

Fletcher et al., Br. J. Cancer 2003; 88:579-85.*
Persson et al., Mol. Phylogenetics & Evolution, 2005; 36:734-40.*
Chevet et al., Oncogene, 2013; 32:2499-2509.*
Obacz et al., Eur. J. Cell Biol., 2015; 94:139-147.*
Chen & Xie, Int'l J. Nanomedicine, 2012; 7:3971-80.*
Ozpolat et al., J. Internal Med. 2009; 267:44-53.*
Ogris & Wagner, Human Gene Therapy 2011; 22:799-807.*
Fujita et al., Int. J. Mol. Sci., 2015; 16:5254-5270.*
Wang et al., Lung Cancer, 2011; 287-93.*
Kong et al., Int J Clin Exp Pathol, 2014; 7:7497-7507.*

* cited by examiner

*Primary Examiner* — Jessica H Roark
(74) *Attorney, Agent, or Firm* — Pamela J. Sherwood; Bozicevic, Field & Francis LLP

(57) ABSTRACT

Embodiments are related to processes for using an Anterior Gradient Homolog 3 (AGR3) therapeutic to treat an enhanced AGR2 expressing cancer, or its premalignant precursor, comprising administering an amount of an AGR3 therapeutic to a human patient in need thereof.

5 Claims, 10 Drawing Sheets

| | | | | | | | | | | | | | | | | | | | | | |
|---|---|---|---|---|---|---|---|---|---|---|---|---|---|---|---|---|---|---|---|---|---|
|SEQ ID No. 1| 1|M|E|K|I|P|V|S|A|F|-|L|L|L|V|A|L|S|Y|T|L|A|R|D|T|T|V|K|P|G|A|AGR2|
|SEQ ID No. 2| 1|M|M|L|H|S|A|L|G|L|C|L|L|L|V|T|V|S|-|-|-|-|S|N|L|A|I|A|I|AGR3|

| | | | | | | | | | | | | | | | | | | | | | | |
|---|---|---|---|---|---|---|---|---|---|---|---|---|---|---|---|---|---|---|---|---|---|---|
|30|K|K|D|T|K|D|S|R|P|K|L|P|Q|T|L|S|R|G|W|G|D|Q|L|I|W|T|Q|T|Y|E|AGR2|
|25|K|K|E|K|R|-|-|-|P|P|Q|T|L|S|R|G|W|G|D|D|I|T|W|V|Q|T|Y|E|AGR3|

| | | | | | | | | | | | | | | | | | | | | | |
|---|---|---|---|---|---|---|---|---|---|---|---|---|---|---|---|---|---|---|---|---|---|
|60|E|A|L|Y|K|S|K|T|S|N|K|P|L|M|I|I|H|H|L|D|E|C|P|H|S|Q|A|L|K|K|AGR2|
|50|E|G|L|F|Y|A|Q|K|S|K|K|P|L|M|V|I|H|H|L|E|D|C|Q|Y|S|Q|A|L|K|K|AGR3|

| | | | | | | | | | | | | | | | | | | | | | |
|---|---|---|---|---|---|---|---|---|---|---|---|---|---|---|---|---|---|---|---|---|---|
|90|V|F|A|E|N|K|E|I|Q|K|L|A|E|Q|-|F|V|L|L|N|L|V|Y|E|T|T|D|K|H|L|AGR2|
|80|V|F|A|Q|N|E|E|I|Q|E|M|A|Q|N|K|F|I|M|L|N|L|M|H|E|T|T|D|K|N|L|AGR3|

| | | | | | | | | | | | | | | | | | | | | | |
|---|---|---|---|---|---|---|---|---|---|---|---|---|---|---|---|---|---|---|---|---|---|
|119|S|P|D|G|Q|Y|V|P|R|I|M|F|V|D|P|S|L|T|V|R|A|D|I|T|G|R|Y|S|N|R|AGR2|
|110|S|P|D|G|Q|Y|V|P|R|I|M|F|V|D|P|S|L|T|V|R|A|D|I|A|G|R|Y|S|N|R|AGR3|

| | | | | | | | | | | | | | | | | | | |
|---|---|---|---|---|---|---|---|---|---|---|---|---|---|---|---|---|---|---|
|149|L|Y|A|Y|E|P|A|D|T|A|L|L|L|D|N|M|K|K|A|L|K|L|L|K|T|E|L|AGR2|
|140|L|Y|T|Y|E|P|R|D|L|P|L|L|I|E|N|M|K|K|A|L|R|L|I|Q|S|E|L|AGR3|

FIG. 2

| Pathology | AREG positive (%) | AREG positive (%) |
|---|---|---|
| Adenocarcinoma without associated Barrett's esphagus | 21/32 (66) | 32/32 (100) |
| Adenocarcinoma with associated Barrett's esophagus | 32/38 (84) | 38/38 (100) |
| Barrett's esophagus without dysplasia | 26/26 (100) | 26/26 (100) |
| Barrett's esophagus with dysplasia | 18/18 (100) | 18/18 (100) |

FIG. 3

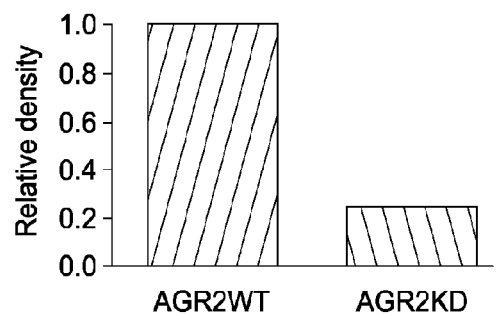
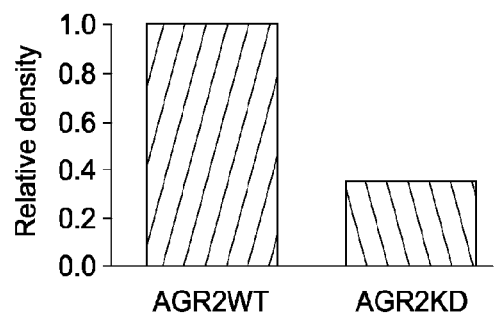
FIG. 5A
FIG. 5B
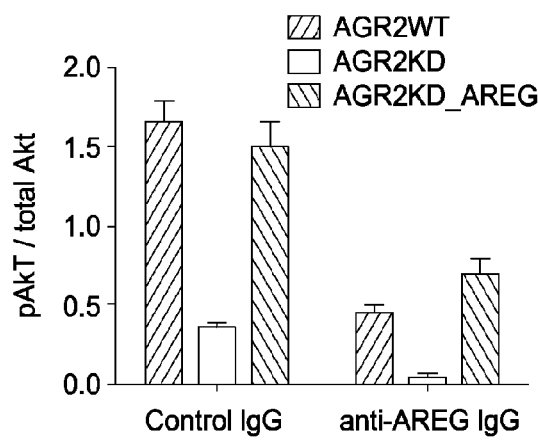
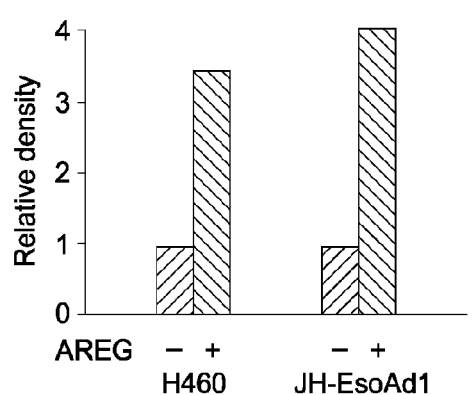
FIG. 5C
FIG. 5D

USE OF AGR3 FOR TREATING CANCER

PRIORITY DATA

This application claims priority to U.S. Ser. No. 61/446,916, filed Feb. 25, 2011.

STATEMENT REGARDING GOVERNMENT SUPPORT

This invention was made with Government support under contract DK063624 awarded by the National Institutes of Health. The Government has certain rights in the invention.

FIELD OF THE INVENTION

The field of the invention is methods for using AGR3 therapeutics to treat cancers, particularly those characterized by enhanced AGR2 expression.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Anterior Gradient Homolog 2 (AGR2) encodes a 17 kDa protein that is highly conserved in vertebrates. In humans, enhanced AGR2 expression was first described in breast cancer, which was followed by similar observations in most human adenocarcinomas, including those derived from the esophagus, pancreas, lung, ovary, and prostate (see, e.g., Hao et al., Gastroenterology, 131:925-33 (2006); Lowe et al., PLoS ONE, 2:e323 (2007); Ramachandran et al., Cancer Res, 68:7811-18 (2008); Thompson and Weigel, Biochem Biophys Res Commun, 251:111-16 (1998); Zhang et al., Genes Chromosomes Cancer, 43:249-59 (2005); Fritzsche et al., Histology and Histopathology, 22:703-08 (2007); Zhu et al., Cancer Lett, 245:303-14 (2007); and Edgell et al., Clin Sci Lond, 118:717-25 (2010)). Although unpublished, it is also known that AGR2 expression is enhanced in colon and stomach adenocarcinoma. Papillary tumors of the thyroid also exhibit high AGR2 expression, and both in vitro and in vivo studies have demonstrated that AGR2 promotes tumor growth and metastasis (Wang et al., Cancer Res, 68:492-97 (2008); Ramachandran et al. (2008), supra; and Liu et al., Cancer Res, 65:3796-05 (2005)). In adenocarcinoma cell lines and non-transformed fibroblasts, AGR2 induces cell proliferation and anchorage-independent growth in soft agar, and human adenocarcinoma cell lines grown in vivo as mouse xenografts result in smaller tumors when AGR2 expression is reduced (Wang et al., (2008), supra; Ramachandran et al. (2008), supra).

Thus given the association of enhanced AGR2 expression with cell proliferation and a variety of cancers, it is of interest in the art to reduce AGR2 expression. The present invention provides methods and compositions that address this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

This invention is directed to a method for treating a cancer characterized by enhanced AGR2 expression or its premalignant precursor in a subject, comprising: identifying a subject with an enhanced AGR2 expressing cancer; and administering an effective amount of a therapeutic comprising AGR3 to said subject.

In some embodiments, the therapeutic comprises an AGR3 polypeptide, and in some aspects of this embodiment, the AGR3 polypeptide is at least 75% homologous to SEQ ID No. 2, at least 80% homologous to SEQ ID No. 2, at least 85% homologous to SEQ ID No. 2, at least 90% homologous to SEQ ID No. 2, at least 93%, 94%, 95%, 96%, 97%, 98% or 99% homologous to SEQ ID No. 2.

In some embodiments, the AGR3 polypeptide is PEGylated, and in addition or as an alternative, the AGR3 polypeptide may be encapsulated in nano- or microparticles. In some aspects of this embodiment, the nano- or microparticles are selected from liposome nanoparticles, polymer-drug conjugate nanoparticles, polymeric nanoparticles, micelle nanoparticles, dendrimer nanoparticles, polymersome nanoparticles, protein nanoparticles, inorganic nanoparticles, or biological nanoparticles.

In some embodiments, the AGR3 polypeptide therapeutic comprises cell-penetrating peptides, and in preferred embodiments, the cell-penetrating polypeptides target the AGR3 polypeptide to the endoplasmic reticulum. In some aspects, the cell-penetrating peptides are selected from one or more of Tat, penetratin, transportan, oligoarginine, model amphipathic model peptides, MPG or MPGα.

In yet other embodiments, the therapeutic comprises an AGR3 polynucleotide. In some aspect of this embodiment, the AGR3 polynucleotide therapeutic comprises a nonviral vector and in other aspects of this embodiment, the therapeutic comprises a viral vector. In some aspects, the viral vector is derived from a retrovirus, a lentivirus, an adenovirus, an adeno-associated virus, or a herpes virus.

In some aspects the AGR3 polynucleotide therapeutic comprises one or more of polyamine, polycationic lipids or polymers. Also, in some embodiments, the AGR3 polynucleotide or polypeptide therapeutic comprises one or more molecules that target cell surface markers associated with cancers characterized by enhanced AGR2 expression or its premalignant precursor, such as one or more of CD57, CD44, CD24, ESA, ABCG2, TROP2, CA125 or CD4.

In some embodiments, the AGR3 polynucleotide codes for an AGR3 polypeptide that comprises a cell penetrating peptide; and in preferred embodiments, the cell-penetrating polypeptides target the AGR3 polypeptide to the endoplasmic reticulum.

In some embodiments, the methods further comprise the step of monitoring AGR2 expression in the subject at one or more time points post-administration of the therapeutic comprising an AGR3.

Other embodiments of the invention provide a method for reducing the expression of AGR2 in a cancer characterized by enhanced AGR2 expression or a premalignant precursor thereof, comprising administering an effective amount of a therapeutic comprising AGR3 peptide or an AGR3 polynucleotide that codes for an AGR3 peptide. Yet other embodiments of the invention comprise formulations of AGR3 polynucleotide or polypeptide therapeutics.

These and other aspects and uses of the invention will be described in the detailed description.

BRIEF DESCRIPTION OF THE FIGURES

FIG. 2 is a protein sequence alignment of human AGR2, initially named hAG-2, and human AGR3, initially named hAG-3 (DNAStar MegAlign program—Jotun Hein alignment).

FIG. 3 is a table of results of pathological analysis of AGR2 and amphiregulin (AREG) protein expression in esophageal adenocarcinoma cells.

FIGS. 5A through 5D are bar graphs showing results of studies demonstrating AGR2 regulates EGFR and AKT phosphorylation through amphiregulin (AREG).

DETAILED DESCRIPTION OF THE INVENTION

Figure 1:
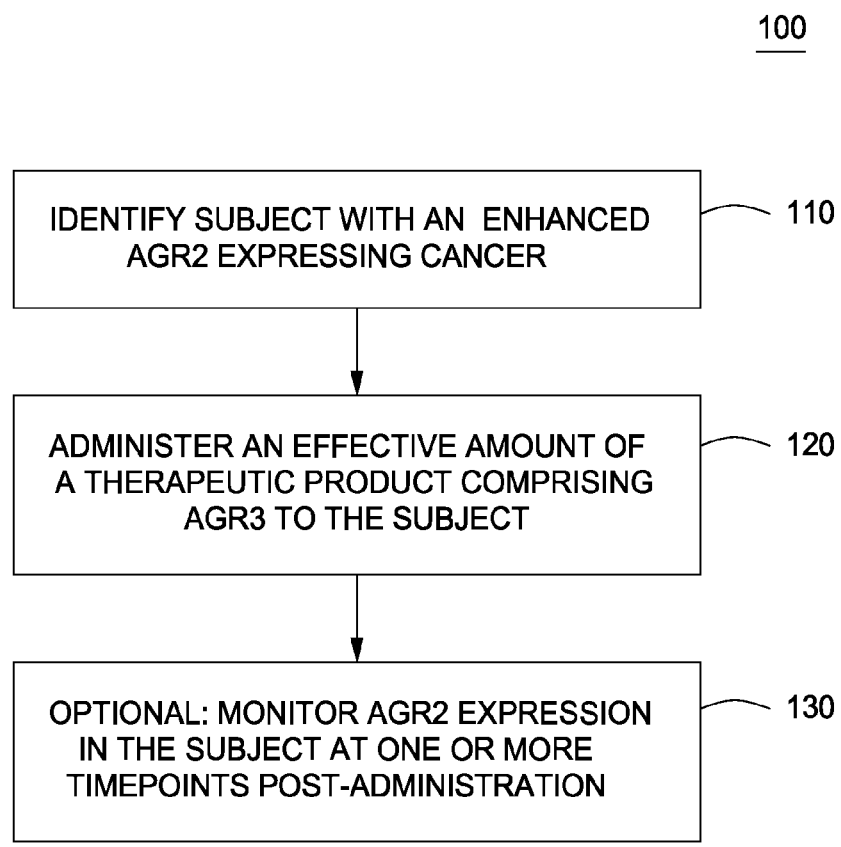
FIG. 1 provides a simplified flow chart of one embodiment of one method of the invention.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Specific illustrations of suitable techniques can be had by reference to the examples herein. However, other equivalent conventional procedures can, of course, also be used. Such conventional techniques and descriptions can be found in standard laboratory manuals such as Chow, et al., (2008), *Using Animal Models in Biomedical Research* (World Scientific Publishing Co.); Weir and Blackwell (Eds.), *Handbook of Experimental Immunology*, Vols. I-IV (Blackwell Scientific Publications); Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), Lehninger, *Principles of Biochemistry* $3^{rd}$ Ed., W.H. Freeman Pub., New York, N.Y.; and Berg et al. (2002) *Biochemistry*, $5^{th}$ Ed., W.H. Freeman Pub., New York, N.Y., all of which are herein incorporated in their entirety by reference for all purposes. Before the present compositions, research tools and methods are described, it is to be understood that this invention is not limited to the particular methods, compositions, targets and uses described, as such may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a composition" refers to one or mixtures of such compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes both of the limits, ranges excluding either of those included limits are also included in the invention.

In the following description, numerous specific details are set forth to provide a more thorough understanding of the present invention. However, it will be apparent to one of skill in the art upon reading the specification that the present invention may be practiced without one or more of these specific details. In other instances, well-known features and procedures well known to those skilled in the art have not been described in order to avoid obscuring the invention.

DEFINITIONS

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

"Anterior Gradient Homolog 3" or "AGR3 protein" or "AGR3" or the like refers to a polypeptide of mammalian origin, e.g., mouse or human AGR3, with a sequence substantially similar to that of SEQ ID No. 2 (see FIG. 2) or, as context requires, a polynucleotide encoding such a polypeptide, and has at least one of the following features: (1) an amino acid sequence of a naturally occurring mammalian AGR3 polypeptide, or a fragment thereof; (2) an amino acid sequence substantially identical to, e.g., at least 70%, 75%, 80%, 85%, 90%, 95%, 98%, or 99% identical to, an amino acid sequence encoding a naturally occurring mammalian AGR3 polypeptide, or a fragment thereof; (3) an amino acid sequence that is encoded by a naturally occurring mammalian AGR3 nucleotide sequence, or a fragment thereof; (4) an amino acid sequence encoded by a nucleotide sequence degenerate to a naturally occurring mammalian AGR3 nucleotide sequence, or a fragment thereof; or (5) an amino acid sequence encoded by a nucleotide sequence that hybridizes under medium or high stringency conditions to a naturally occurring mammalian AGR3 nucleotide sequence, or a fragment thereof. In some embodiments, the term possesses the additional feature of having substantially the activity of human AGR3 in its ability to reduce the expression of AGR2 or AREG in a bioassay, where reduce does not mean 100%, but rather anywhere from 1% to 100%. By fragment is meant an active fragment, that is to say, a fragment having substantially the activity of full-length human AGR3 in its ability to reduce the expression of AGR2 or AREG in a bioassay, where reduce does not mean 100%, but rather anywhere from 1% to 100%. In addition, the term "Anterior Gradient Homolog 3" or "AGR3 protein" or "AGR3" or the like also includes small chemical molecules or peptides that mimic the structure of AGR3.

A "coding sequence" of AGR3 or a sequence that "encodes" an AGR3 peptide is a nucleic acid molecule that is transcribed (in the case of DNA) and translated (in the case of mRNA) into an AGR3 polypeptide in vivo when placed under the control of appropriate control sequences. The boundaries of the coding sequence are determined by a start codon at the 5' (amino) terminus and a translation stop codon at the 3' (carboxy) terminus.

The term DNA "control sequences" refers collectively to promoter sequences, polyadenylation signals, transcription termination sequences, upstream regulatory domains, origins of replication, internal ribosome entry sites, enhancers, and the like, which collectively provide for the replication, transcription and translation of a coding sequence in a recipient cell. Not all of these types of control sequences need to be present so long as the selected AGR3 coding sequence is capable of being replicated, transcribed and translated in an appropriate host cell.

The terms "effective amount" or "therapeutically effective amount" of an AGR3 therapeutic composition used in the methods of the invention refer to a nontoxic but sufficient amount of the therapeutic composition to provide the desired response, such as eliminating cancer cells, stopping the growth of cancer cells, prolonging remission of cancer, etc. The exact amount of an AGR3 therapeutic required to be an effective amount will vary from subject to subject, depending on the age and general condition of the subject, the severity (stage) of the cancer being treated, and the particular therapeutic to be delivered, mode of administration, and the like. Dosage parameters for the present methods are provided herein; however, optimization of an appropriate "effective" amount in any individual case may be determined by one of ordinary skill in the art using the methods set forth herein and routine experimentation.

"Operably linked" refers to an arrangement of elements where the components so described are configured so as to perform their usual function. Thus, control sequences operably linked to a coding sequence are capable of effecting the expression of the coding sequence. The control sequences need not be contiguous with the coding sequence so long as they function to direct the expression thereof. Thus, for example, intervening untranslated yet transcribed sequences can be present between a promoter sequence and the coding sequence and the promoter sequence can still be considered "operably linked" to the coding sequence.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase I, II or III.

The terms "subject", "individual" or "patient" may be used interchangeably herein and refer to a mammal, preferably a human.

The term "therapeutic composition" or "therapeutic AGR3 composition" as used herein refers to a composition comprising an AGR3 protein or peptide or comprising a polynucleotide capable of expressing an AGR3 protein or peptide that has the ability to retard or stop growth of adenocarcinoma or other cancer cells or otherwise extends the life of a subject with cancer as measured in any of the known animal models or by assessment performed in humans including those described herein.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; or (c) relieving the disease, e.g., causing regression of the disease, e.g., to completely or partially remove symptoms of the disease.

A "vector" is a replicon, such as plasmid, phage, viral construct or cosmid, to which another DNA segment may be attached. Vectors are used to transduce and express the DNA segment in cell.

The Invention in General

Anterior Gradient Homolog 3 (AGR3) is a homologue in the AGR2 family of proteins for which a function has not been determined. FIG. 1 is a simplified flow diagram of one embodiment of a method 100 of the present invention. In a first step 110, a subject with an enhanced AGR2 expressing cancer, such as adenocarcinoma, is identified. In a second step 120, an effective amount of an AGR3-based therapeutic is administered to the subject identified in step 110. In an optional step 130, AGR2 expression is monitored in the subject at one or more timepoints following administration of the AGR3-based therapeutic to determine, e.g., whether additional treatment is necessary. As an alternative or in addition, tumor viability and/or growth also optionally may be monitored to determine, e.g., whether additional treatment is necessary.

FIG. 2 shows the protein sequence alignment of human AGR3, initially named hAG-3, and human AGR2, initially named hAG-2 (see, e.g., Fletcher et al., Br J Cancer, 88:579-85 (2003)). The boxed regions on the AGR3 sequence indicate exact amino-acid matches of AGR3 with AGR2. Overall, both proteins show 71% similarity (Jotun-Hein method, 64% identity by BLASTP) with the majority of differences being in the hydrophobic leader signal sequences (the AGR2 signal peptide is amino acid 1 to 20, and the AGR2 mature protein is amino acid 21 to 175).

Identifying Enhanced AGR2 Expressing Cancers and Premalignant Precursors

DNA microarray, quantitative PCR, Western blotting, suppression subtractive hybridization, Northern blotting, immunohistochemistry, comparative genomic hybridization followed by quantitative PCR, ELISA, and like techniques are techniques well known in the art and have been used in bioassays to identify AGR2 expressing cancers and their premalignant precursors. Most human adenocarcinomas, including those derived from the esophagus, pancreas, lung, ovary, and prostate have been identified as being cancers characterized by enhanced AGR2 expression. For example see Hao et al., Gastroenterology, 131:925-33 (2006) (DNA microarray, quantitative PCR, in situ hybridization); Lowe et al., PLoS ONE 2:e323 (2007) (DNA microarray, immunohistochemistry, in situ hybridization); Ramachandran et al., Cancer Res, 68:7811-18 (2008) (quantitative PCR, immunohistochemistry, and Western blotting); Thompson and Weigel, Biochem Biophys Res Commun, 251:111-16 (1998) (suppression subtractive hybridization and Northern blotting); Zhang et al., Genes Chromosomes Cancer, 43:249-(2005) (suppression subtractive hybridization, Western blotting, and immunohistochemistry); Fritzsche et al., Histology and Histopathology, 22:703-08 (2007) (immunohistochemistry); Zhu et al., Cancer Lett, 245:303-14 (2007) (comparative genomic hybridization followed by quantitative PCR); and Edgell et al., Clin Sci Lond, 118: 717-725 (2010) (ELISA). Such techniques and others may be used to identify additional cancers characterized by enhanced AGR2 expression. Further, these same techniques may be used to monitor the effectiveness of AGR3 treatment on the AGR2 expressing cancers or premalignant precursors being treated (optional step 130 in FIG. 1).

AGR3 Therapeutics

Anterior Gradient Homolog 3 or AGR3 therapeutics or the like refers to a therapeutic comprising a polypeptide of mammalian origin, such as a mouse or human AGR3, with a sequence substantially similar to that of SEQ ID No. 2 (see FIG. 2) or, as context requires, a polynucleotide encoding such a polypeptide.

AGR3 Peptide Therapeutics

Although therapeutic proteins are highly potent endogenous substances, they are generally susceptible to proteolytic degradation, aggregation, polymerization, and adsorption onto foreign surfaces. In addition, most proteins have short biological half-lives and often induce immunogenic responses when administered into the body. For administration, the AGR3 therapeutic composition in a formulation may be complexed or bound to a polymer to increase its circulatory half-life; however, in making such modifications, care must be taken to assure that the AGR3 therapeutic is able to enter the target cancer cell. Results of experiments conducted thus far indicate that expression of AGR3 in normal (i.e., non-cancer) cells has no detectable effect; thus, designing an AGR3 therapeutic that targets more than one or many cell types is not problematic. Examples of polymers useful for this purpose include polyethylene polyols and polyoxyethylene polyols such as polyoxyethylene glycerol, polyethylene glycol (PEG), polyoxyethylene sorbitol, polyoxyethylene glucose, or the like. The glycerol backbone of polyoxyethylene glycerol is the same backbone occurring in, for example, animals and humans in mono-, di-, and triglycerides. PEG is a linear or branched polyether terminated with hydroxyl groups that is synthesized by anionic ring opening polymerization of ethylene oxide. The molecular weights of linear PEGs available for biomedical applications usually range between a few hundred to several tens of thousands of daltons.

The PEG polymer employed need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1-C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

The therapeutic compounds can optionally be covalently bonded via one or more of the amino acid residues of the therapeutic compound to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the therapeutic agent. It will be understood, however, that the type and amount of the reactive group chosen, as well as the type of polymer employed, to obtain optimum results, will depend on the particular AGR3 therapeutic compound employed to avoid having the reactive group react with too many particularly active groups on the AGR3 therapeutic compound. As this may not be possible to avoid completely, it is recommended that generally from about 0.1 to 1000 moles, preferably 2 to 200 moles, of activated polymer per mole of protein, depending on protein concentration, is employed. The final amount of activated polymer per mole of protein is a balance to maintain optimum activity, while at the same time optimizing, if possible, the circulatory half-life of the protein.

While the residues may be any reactive amino acids on the protein, such as a cysteine or the N-terminal amino acid group, preferably the reactive amino acid is lysine, which is linked to the reactive group of the activated polymer through its free epsilon-amino group, or glutamic or aspartic acid, which is linked to the polymer through an amide bond.

The covalent modification reaction may take place by any appropriate method generally used for reacting biologically active materials with inert polymers, preferably at about pH 5-9, more preferably 7-9 if the reactive groups on the AGR3 therapeutic compound are lysine groups. Generally, the process involves preparing an activated polymer (with at least one terminal hydroxyl group), preparing an active substrate from this polymer, and thereafter reacting the therapeutic agent with the active substrate to produce the therapeutic agent suitable for formulation. The above modification reaction can be performed by several methods, which may involve one or more steps. Examples of modifying agents that can be used to produce the activated polymer in a one-step reaction include cyanuric acid chloride (2,4,6-trichloro-5-triazine) and cyanuric acid fluoride.

In one embodiment the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the therapeutic agent. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100-110° C. for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxypolyethylene glycolyl-N-succinimidyl glutarate, which can then be reacted with the therapeutic agent. This method is described in detail in Abuchowski et al., Cancer Biochem. Biophys., 7:175-186

(1984). In another example, the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., Peptides: Synthesis-Structure-Function, Proceedings of the Seventh American Peptide Symposium, Rich et al. (eds.) (Pierce Chemical Co., Rockford Ill., 1981), p. 97-100, and in Nitecki et al., High-Technology Route to Virus Vaccines (American Society for Microbiology: 1986) entitled "Novel Agent for Coupling Synthetic Peptides to Carriers and Its Applications." Other specific methods of producing therapeutic peptide conjugated to PEG include the methods described in U.S. Pat. No. 4,179,337 and U.S. Pat. No. 4,935,465, which discloses PEG reversibly but covalently linked to therapeutic peptides.

When developing a biopharmaceutical product a wide range of formulation components have to be considered; these include buffer type and strength, use of ionic compounds, sugars, polyols and certain amino acids, the incorporation of surfactants, inclusion of antioxidants, chelating agents and other substances. The stability of many proteins/peptides can be enhanced by the exclusion of water from the product. Freeze-drying is most often employed for this purpose, but spray drying, drying by means of supercritical fluid processing and precipitation have also been investigated. Freeze-drying does not always result in a more stable product compared with a solution. Proteins/peptides can denature during freezing because of changes in the microenvironment; for instance, from increasing salt concentration or changing pH in the unfrozen liquid. Aggregation and denaturation can also occur during the secondary drying process as a result of the loss of residual water. The rate of freezing has also been found to affect the formation of aggregates. Denaturation during spray drying has been reported as a result of the high air-product interfaces and high temperatures during drying. The supercritical fluid technique may involve high pressure, high air-product interfaces and possibly solvents, all of which can cause denaturation. Residual moisture in the product can cause both chemical and physical degradation, which, apart from reduced bioactivity, can also cause reduced reconstitution and diffusional properties.

A variety of excipients can be introduced into a formulation in an effort to increase the stability of the protein/peptide during the manufacture, handling and delivery of the product. For example, sugars have been shown to protect proteins/peptides against denaturation and are particularly used as cryoprotectants. The mechanism for stabilization is similar in both liquid and frozen systems. The presence of a sugar creates a thermodynamically unfavorable condition, because the chemical potential—the partial molar free energy for both the protein/peptide and the sugar—is increased. Preferential exclusion of the sugar from the surface of the protein/peptide minimizes thermodynamic activity, which in turn preserves the preferred conformation. Sugars may, however, not be universally suitable for all conditions. Temperature-dependent hydrophobic interactions between a protein/peptide and certain sugars may cause preferential binding at higher temperatures, thus decreasing the activity of a protein/peptide. For optimum long-term stability, disaccharides such as trehalose and sucrose are recommended by the literature. A thorough discussion of pharmaceutically acceptable diluents/excipients is available in Remington: *The Science and Practice of Pharmacy* (21st ed., Lippincott Williams & Wilkins (2005)).

Reducing sugars can convert amide groups to ketoamine groups, resulting in a brown color of the product. Nonreducing sugars should, therefore, preferentially be used for tonicity adjustments and as stabilizers. Sugars useful in the present invention may include trehalose, sucrose, maltose, fructose, raffinose, lactose, or glucose.

Polyols useful in AGR3 formulations include polyhydric alcohols and carbohydrates such as cyclodextrins, mannitol, sorbitol, glycerol, xylitol, and inositol. Polyols are used to stabilize proteins/peptides both in solution and on freeze-drying, and are particularly useful in preventing denaturation. Some of the materials in this group, such as glycerol, stabilize proteins/peptides through selective solvation of the protein/peptide causing water molecules to pack more closely around the protein/peptide to exclude the more hydrophobic additive. At higher solvent concentration, the polyols may denature the protein/peptide. Cyclodextrins may prevent aggregation by molecular encapsulation.

Surfactants are often added to stabilize proteins/peptides, and both nonionic and anionic surfactants have been used including poloxamer 407, poloxamer 188, polysorbate 80, polysorbate 20, octoxynol-9, polyoxyethylene-(23) lauryl alcohol, polyoxyethylene-(20) oleyl alcohol, and sodium lauryl sulphate. The addition of surfactants may prevent adsorption of proteins/peptides to surfaces, reduce agitation-induced aggregation, and reduce denaturation. Reports have suggested that surfactants are less effective in protecting against thermally induced denaturation. The addition of surfactants has also been used to prevent freezing or freeze thaw-induced aggregation as well as delivery device-induced aggregation. Some studies investigating the effect of surfactant concentration on protein/peptide aggregation suggested that the protective action coincides with the critical micelle concentration (CMC) for the surfactant, supporting the theory of the formation of a surfactant monolayer at the air-water interface being their mechanism of action. For other surfactants the maximum protective effect occurs at concentrations much higher than the CMC, indicating that other factors are also involved. Higher concentrations of surfactants may destabilize a protein/peptide. The concentration required to protect a protein/peptide should, therefore, be evaluated for each possible encountered stress. Surfactants commonly used to prevent adsorption, aggregation, precipitation, denaturation and freeze-thaw stresses are given in the table.

Amino acids such as glycine, arginine, alanine, proline, aspartic acid, glutamic acid, and lysine have been added to biopharmaceuticals for a variety of reasons; dicarboxylic amino acids such as aspartic and glutamic acid have been used to reduce aggregation, and glycine, arginine and lysine have also been reported to prevent aggregation. In addition, amino acids have been found to be useful as chelating agents, and may reduce surface adsorption. They have also been reported to increase the thermal stability of proteins/peptides.

Low concentrations of poly(vinylpyrollidone) (PVP) have been successfully used to inhibit antibody aggregation, whereas PVP concentrations greater than 1% have been shown to enhance antibody aggregation. Dextran is commonly used in freeze-dried products as a cryostabilizer when it is necessary to raise the collapse temperature of a formulation. Other excipients from this group include polyethylene glycol.

Ionic compounds such as salts (sodium sulphate, ammonium sulphate, magnesium sulphate, sodium acetate, sodium lactate, sodium succinate, sodium proprionate, and potassium phosphate) and buffers interact with proteins/peptides via non-specific or specific binding. Depending on the type of interaction, a salt may increase thermal stability, increase the solubility and reduce the extent of aggregation.

Chelating agents and antioxidants are mainly used to prevent chemical degradation and include EDTA, tris(hydroxymethyl)aminomethane (TRIS), diethylenetriaminepentaacetic acid, inositol, hexaphosphate, ethylenediaminebis (O-hydroxyphenylacetic acid), and desferal and ascorbic acid and glutathione. Lipids and fatty acids or their derivatives are used to stabilize proteins/peptides and nucleic acids, which is not surprising as many amino acid chains in circulation are known to bind to lipids. Stabilization by fatty acids or their derivatives, in particular phospholipids, results from the association of their polar and non-polar portions with reacting groups on the protein/peptide or nucleic acid.

Alternatively or in addition to PEGylation or other protein or peptide modifications, nano- or microparticle technology may be employed as a delivery vehicle for the AGR3 peptide therapeutic or for delivery of the AGR3 polynucleotide therapeutics described infra. Nanoparticles as vehicles or drug delivery systems enable unique approaches for drug treatment. Nanoscale drug delivery vehicles have shown the ability to encapsulate a variety of therapeutic agents such as peptides, proteins, and nucleic acids. By encapsulating these molecules inside a nanocarrier, the solubility and stability of the drugs can be improved, providing an opportunity to reevaluate potential drugs previously ignored because of poor pharmacokinetics. Encapsulated molecules can be released from nanocarriers in a controlled manner over time to maintain a drug concentration within a therapeutic window or the release can be triggered by some stimulus unique to the delivery site. The surface of the nanocarrier can be engineered to increase the blood circulation half-life and influence the biodistribution, while attachment of targeting ligands to the surface can result in enhanced uptake by target tissues. The small size allows nanocarriers to overcome biological barriers and achieve cellular uptake. The net result of these properties is to lower the systemic toxicity of the therapeutic agent while increasing the concentration of the agent in the area of interest, resulting in a higher therapeutic index for the therapeutic agent.

One group of nanoparticles are liposome nanoparticles. Lipids form nanoparticle vesicles through the self-assembly of amphiphilic lipids and excipients. The lipids form a bilayer based on hydrophobic interactions in continuous parallel packing, with the hydrophilic head groups positioned towards the aqueous environment. Hydrophilic molecules can be encapsulated in the inner aqueous phase while hydrophobic molecules can be carried in the hydrophobic domains of the lipid bilayer. Physicochemical properties of liposomes can be precisely changed to control surface charge, functionality, and size by simply mixing commercially available lipid molecules. This offers a significant advantage over other carriers that require much more controlled synthesis steps and additional chemical modifications. Generally, lipids used to prepare vesicular formulations are found in the human body and approved by the FDA, such as DSPE (1,2-distearoyl-sn-glycero-3-phosphoethanolamine), HSPC (hydrogenated phosphatidylcholine from soybean lecithin), EggPG (egg yolk phosphatidylglycerol) and DSPC (1,2-distearoyl-glycero-3-phosphocholine). Each of these lipids can be obtained with or without polyethylene glycol (PEG), which can be used to modify the surface of the resulting liposome.

Another group of nanoparticles are polymer-drug conjugate nanoparticles. Polymer-drug conjugates are formed through side-chain grafting of therapeutics to polymer chains, allowing them to deliver high doses of therapeutics. Although the physicochemical properties of a number of formulations are not disclosed, the size of polymer-drug conjugates is generally below 20 nm. Polyamino acids grafted with drugs on the side chains are another class of polymer-drug conjugates that have demonstrated high drug loading and efficacy.

Yet another group of nano- or micro particles are polymeric nanoparticles. Polymeric nanoparticles provide significant flexibility in design because polymers can be biodegradable or nonbiodegradable, and can be made synthetically or derived from natural sources. To be used successfully as a biodegradable polymer in the controlled drug delivery formulations of the present invention, the material preferably is chemically inert and free of leachable impurities. The polymer must also have appropriate physical characteristics, for example, display minimal undesired aging, be readily processable, and the like.

Biodegradable polymers are typically degraded into individual monomers, which are metabolized and removed from the body via normal metabolic pathways. Some preferred biodegradable polymers include poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), and poly(methacrylic acid). Biodegradable polymers particularly preferred in the present invention include polylactides (PLA), polyglycolides (PGA), poly(lactide-co-glycolides) (PLGA), polyanhydrides, polycaprolactone, poly-3-hydroxybutyrate and polyorthoesters. Such biodegradable polymers have been characterized extensively and can be formulated to exhibit desired degradation properties as (see, e.g., Edlund & Albertsson, Degradable Aliphatic Polyesters, pp. 67-112 (2002), Barman et al., J. of Controlled Release 69:337-344 (2000); Cohen et al., Pharmaceutical Res. (8): 713-720 (1991)). Degradation and drug release kinetics can be precisely controlled by the physicochemical properties of the polymer, such as molecular weight, dispersity index, hydrophobicity, and crystallinity. In general, therapeutics can be released in a controlled manner with first-order kinetics due to drug diffusion through the polymeric matrix or triggered in response to the local environment. The nanoparticle surface is usually sterically stabilized by grafting, conjugating, or adsorbing hydrophilic polymers such as PEG to its surface, which can also reduce hepatic uptake and improve circulation half-life.

In one particular embodiment of the invention, the polymer comprises poly(lactide-co-glycolides) (PLGA). PLGA is a copolymer which has been used in a host of FDA approved therapeutic devices, owing to its biodegradability and biocompatibility. PLGA is synthesized by means of random ring-opening co-polymerization of two different monomers, the cyclic dimers (1,4-dioxane-2,5-diones) of glycolic acid and lactic acid. Common catalysts used in the preparation of this polymer include tin(II) 2-ethylhexanoate, tin(II) alkoxides, or aluminum isopropoxide. During polymerization, successive monomeric units of glycolic or lactic acid are linked together in PLGA by ester linkages, thus yielding a linear, aliphatic polyester as a product.

Depending on the ratio of lactide to glycolide used for the polymerization, different forms of PLGA can be obtained: these are usually identified in regard to the monomers' ratio used (e.g., PLGA 75:25 identifies a copolymer whose composition is 75% lactic acid and 25% glycolic acid). PLGA degrades by hydrolysis of its ester linkages in the presence of water. It has been shown that the time required for degradation of PLGA is related to the monomers' ratio used in production: the higher the content of glycolide units, the lower the time required for degradation. An exception to this rule is the copolymer with 50:50 monomer ratio which exhibits a faster degradation (about two months). In addition, polymers that are end-capped with esters (as opposed to the free carboxylic acid) demonstrate longer degradation half-lives. Alternatively, the AGR3 therapeutic may be encapsulated in batches of microparticles having different release profiles; for example, 10% of the AGR3 therapeutic to be delivered may be encapsulated in microparticles having, e.g., a one day to four week release profile; 30% of the AGR3 therapeutic to be delivered may be encapsulated in microparticles having, e.g., a three week to six week release profile; 30% of the AGR3 therapeutic to be delivered may be encapsulated in microparticles having, e.g., a six week to ten week release profile; and 30% of the AGR3 therapeutic to be delivered may be encapsulated in microparticles having, e.g., an eight week to twelve week release profile. In yet another example, the AGR3 therapeutic may be encapsulated where 20% of the AGR3 therapeutic to be delivered may be encapsulated in microparticles having, e.g., a one day to two week release profile; 20% of the AGR3 therapeutic to be delivered may be encapsulated in microparticles having, e.g., a one week to five week release profile; 20% of the AGR3 therapeutic to be delivered may be encapsulated in microparticles having, e.g., a four week to eight week release profile; 20% of the AGR3 therapeutic to be delivered may be encapsulated in microparticles having, e.g., a six week to ten week release profile and 20% of the AGR3 therapeutic to be delivered may be encapsulated in microparticles having, e.g., an eight week to twelve week release profile. In such embodiments, a single type of biodegradable polymer may be used, but used in formulations with different release profiles; alternatively, different biodegradable polymers having different release characteristics may be used. In yet another embodiments, the formulation of the microparticles may be varied so as to change the surface of the microparticles to enhance or retard, as desired, the delivery of the AGR3 therapeutic composition through the body.

Micelle nanoparticles are composed of lipids or other amphiphilic molecules, such as polymers or polyamino acids, and self-assemble into small nanoparticles composed of a hydrophobic core. Micelles have been developed as drug delivery carriers for hydrophobic drugs. Micelle systems are also being developed for the delivery of a myriad of therapeutic agents using formulations with sizes ranging from 10 to 200 nm using polyamino acids and synthetic polymers.

Dendrimer nanoparticles are globular macromolecules (5-10 nm) with well-defined branching architectures and surface functional groups available for further modification. The multifunctional capabilities possible through controlled synthesis methods are leading to new classes of dendrimers that can carry therapeutic molecules, diagnostic agents, and targeting molecules. Dendrimers have remarkable molecular monodispersity and suitable pharmacokinetic properties for systemic drug delivery with cleavable chemistry for drug dissociation. Amphiphilic dendrimers are able to form micelles by self-assembly with hydrophilic groups on the surface for functionalization. Drug release kinetics are controlled through the properties of the polymer chains, which can be designed to be degraded for release of a payload.

Another group of nano- or microparticles are polymersome nanoparticles. Polymersomes have a structure similar to liposomes, but are composed of synthetic polymer/polypeptide amphiphiles and self-assemble to form polymer shell vesicles (~100 nm) when hydrated and extruded. Polymersomes show higher stability and lateral fluidity than liposomes and the release is triggered by the degradation of the polymer chain and destabilization of the shell layer.

Yet another group of nanoparticles are protein nanoparticles. Protein-based drug delivery systems have recently made a big impact with albumin-bound drug nanoparticles (~130 nm). The approval of albumin-bound paclitaxel (Abraxane, ABI-008) in January 2005 by the Food and Drug Administration (FDA) for metastatic breast cancer therapy as well as multiple clinical trials currently in progress for other types of cancer has demonstrated the possibility of using protein-based nanoparticles for delivery of therapeutic agents.

Biological nanoparticles are unicellular microorganisms with different shapes and sizes that encapsulate essential components of the cytoplasm as well as hydrophobic and hydrophilic molecules. One example of biological nanoparticles being evaluated for cancer therapy is a drug delivery system developed by EnGeneIC Pty Ltd called a "nanocell", which consists of anucleate globular bacteria (~400 nm). At present the potential for an immunological response to the carrier due to the presence of lipopolysaccharide (LPS) limits the wide-spread use of biological nanoparticles.

Surface properties and functionalities of gold and other inorganic nanoparticles have been used for the delivery of surface-bound therapeutics.

Hybrid nanoparticles are recently developed nanocarriers that combine advantages from existing systems with well-characterized properties to form lipid-polymer nanoparticles and solid liposomal nanoparticles. Hybrid nanoparticles are composed of at least two different materials to form the core and the corona structure. In general, metallic and polymeric materials form the core and are coated with a single or multiple lipid layers to form a protecting membrane (corona) similar to a liposome or micelle.

Another technology useful in the delivery of AGR3 protein or peptide therapeutics is the use of cell-penetrating peptides. The seminal discoveries that peptides derived from glycoproteins embedded in the lipid envelope of viruses such as HIV virus as well as those derived from the homeodomain of certain transcription factors can directly translocate across the plasma membrane of mammalian cells have opened up new avenues in macromolecular drug delivery. In general, these "cell-penetrating peptides (CPPs)" are basic amino acids causing a net positive charge at physiological pH. In a first attempt to define a peptide as a CPP the following definition was established: CPPs consist of less than 30 amino acids; CPPs are internalized by cells; and CPPs are able to mediate the delivery of a cargo such as a peptide, protein, or nucleic acid. A cargo can be bound to the CPP covalently or non-covalently. Covalent attachment can be achieved either by expression as a fusion construct or by chemical coupling. In some cases, cargo and carrier bind each other non-covalently through ionic interactions. The most prominent examples of CPPs are tat48-60 (Vives et al., JBC, 272:16010-17 (1997)); penetratin (Derossi et al., JBC, 269:10444-50 (1994)); transportan (Pooga et al., FASEB J, 12:67-77 (1998)); TP10 (Soomets et al., Biochim Biophys Acta, 1467: 165-67 (2000)); oligoarginine (Futaki et al., JBC, 276:5836-40 (2001)); MAP (Steiner et al., J. Chromatog., 586:43-50 (1991)); MPG (Morris et al., NAR, 25:2730-36 (1997)); and MPGα (Deshayes et al., Biochemistry 43:7698-06 (2004)).

Particularly of interest for use in the methods of the invention are AGR3 therapeutic formulations comprising CPPs that target the AGR3 therapeutic to the cellular endoplasmic reticulum. See, e.g., Shen et al., Molec. Thera., 19(5):903-12 (2011), describing fusion proteins containing secretory signal peptides; and Flinterman et al., Molec. Thera., 17(2):334-42 (2009), describing modified HIV-1 transactivator (Tat) peptides (described below), both of which are incorporated herein for all purposes.

The ability of the HIV-1 transactivator protein (Tat) to penetrate cellular membranes was first discovered in 1988.

By testing different truncated versions of Tat, Vives et al. revealed that Tat48-60 had the highest transfection efficiency; however, an even shorter peptide almost exclusively composed of basic amino acids (Tat49-57) proved to be essential and sufficient for nuclear import in mammalian cells (see Wender et al., PNAS USA 97:13003-08 (2000)). Tat, its translocation efficiency strongly depends on certain basic residues.

Penetratin, formerly termed pAntp43-58, is a peptide derived from the third helix of the *Drosophila melanogaster* Antennapedia homeodomain protein. It is one of the most widely-investigated CPPs and demonstrates a low toxicity and a high translocation rate.

Transportan, a chimeric 27 amino acid peptide. It is composed of the N-terminal amino acids of the neuropeptide galanin, coupled to mastoparan, a peptide from wasp venom that strongly interacts with membranes. Trimming down transportan led to TP10, a peptide with 21 residues displaying similar properties as the initial peptide.

Microscopic studies performed by Futaki et al. revealed that oligoarginines and other arginine-rich peptides are efficiently taken up by cells. The molecule with the highest efficiency turned out to be octaarginine (R8), whereas peptides of <5 and >12 arginine residues showed only negligible translocation. A direct comparison of nonamers composed of arginine, histidine, lysine or ornithine revealed that arginine residues were most effective in penetrating the plasma membrane because of their guanidinium group.

Model amphipathic peptides (MAP or KLA peptides) are derived from the α-helical amphipathic model peptides.

MPG is a 27 amino acid peptide composed of a hydrophobic domain derived from the N-terminal fusion sequence of the HIV-1 glycoprotein 41 and a hydrophilic domain derived from the nuclear localization sequence (NLS) of the SV40 large T-antigen which are linked by a 3 amino acid spacer. More recently, different derivatives of MPG have been described. One such peptide, termed MPGα, differs by 6 amino acids. Further variations in the hydrophobic part of the original MPG sequence led to the Pep-family (see, e.g., Morris et al., Nat. Biotechnol. 19: 1173-1176 (2000)).

AGR3 Nucleic Acid Therapeutics

As an alternative to AGR3 peptide therapeutics, AGR3 polynucleotide or nucleic acid therapeutics that code for an AGR3 peptide may be employed. Gene therapy is defined as any therapeutic procedure in which genes—a DNA expression cassette comprising an AGR3 gene or a polynucleotide coding for an active AGR3 peptide—are intentionally introduced into human cancer cells. In contrast to conventional small molecule drug therapies, which usually have a transient effect on their molecular targets, gene therapy can result in a permanent change to the genetic constitution of the targeted somatic cells. Genes can be delivered directly to target cancer cells in the body (in vivo gene therapy).

Keys to successful gene therapy include the ability to deliver the therapeutic AGR3 polynucleotides accurately, efficiently, and safely into the nucleus of the target cancer cells and the ability thereafter to control its expression of AGR3 in the target cancer cells. Key steps in the gene therapy process are access, binding and entry into target cells, transport across the cytoplasm into the nucleus, and transcription and translation of the therapeutic protein.

Gene delivery vectors are required for successful deployment of the AGR3 expression cassette, and such vectors set the boundaries for what can be attempted in cancer gene therapy. Key elements of a typical vector include an expression cassette that comprises both the therapeutic AGR3 gene and the regulatory elements that control gene expression as well as delivery vehicle such as some of those discussed in relation to AGR3 protein or peptide therapeutics, supra, whose purpose is to protect the vector from nucleases and to transport it to its destination in the nucleus of target cells. Key components of the vehicle may include a surface element that mediates recognition of the target cell surface and elements mediating subsequent penetration into the correctly identified target cell.

The two broad categories of gene delivery vectors are nonviral and viral vectors. Nonviral vectors are based on plasmid DNA that is grown in bacterial hosts such as *Escherichia coli*. Plasmids are circular DNA molecules that carry an antibiotic resistance marker gene and a bacterial origin of replication to facilitate their amplification in *E coli*. A mammalian expression cassette comprising a therapeutic gene with its associated regulatory elements can be inserted into the plasmid. Unfortunately, naked plasmid DNA is susceptible to degradation by nucleases and does not efficiently enter into mammalian cells. However, in some systems such as after intramuscular administration, plasmid DNA can enter into cell nuclei, leading to expression of the plasmid encoded protein. Viral, bacterial, and tumor antigens expressed in this way can provoke a protective or therapeutic immune response, often more efficiently than a corresponding protein-based vaccine. An alternative approach to achieving in vivo gene delivery by using naked plasmid DNA is the so-called hydrodynamic approach, in which the DNA is injected into the circulation in a large volume of fluid. Applying an electric current to the target site (electroporation) can further enhance the efficacy of gene transfer using naked plasmid DNA. However, for more efficient gene delivery to human tissue, plasmid DNA must be incorporated into a fully synthetic gene therapy vector, e.g., using microprojectiles or cationic lipid-protein formations.

Another approach to gene therapy utilizes a "gene gun." With the gene gun approach, DNA is coated onto microscopic gold or tungsten particles (microprojectiles) that are accelerated toward mammalian cells or tissues using a device known as a gene gun. The microprojectiles penetrate the cytoplasmic and nuclear membranes of the target cells and deliver their plasmid DNA cargo to the cell nucleus with reasonable efficiency. This approach may be useful for gene transfer to explanted tumor cells or to easily accessible tissues such as skin where the target site is relatively well circumscribed.

Alternatively or in addition, polyamines, polycationic lipids, or neutral polymers can be complexed with plasmid DNA, leading to charge neutralization (DNA is negatively charged), protection from nuclease digestion, and enhanced internalization into target cells. Many such DNA nanoparticles have been developed for gene transfer applications, but compared to viral vectors nonviral gene transfer efficiencies remain low. New lipids and additional protein-peptide elements incorporated into DNA lipid formulations may enhance solubility, target cell specificity and efficiency of endosomal escape, or transport to the cell nucleus. The nano- and microparticle systems described supra in relation to AGR3 peptide therapeutics may be used in AGR3 polynucleotide therapeutics as appropriate; of particular use are the PLGA polymer microparticles described herein.

In addition to the nonviral gene delivery systems aforementioned, DNA uptake can be enhanced by the application of an electric current to the target cells or tissues (electroporation) or by its incorporation into microbubbles that are then burst in the vicinity of the target cell population by the application of high-frequency ultrasound (ultrasonoporation). Advantages of nonviral vectors include the high genome capacity of 30 to 40 kb and their lack of immunogenicity. An additional advantage relative to viral vectors is the perception of a lower risk of harmful adverse effects. Important disadvantages of nonviral vectors include their relatively low transduction efficiencies and their transient expression profile, which typically peaks within 48 hours but is thereafter rapidly extinguished by 7 days. However, in some situations this may be an advantage, and it may be possible to prolong the expression profile by using plasmid DNA replicons incorporating mammalian origins of replication, e.g., from the Epstein-Barr virus.

Viral vectors provide an alternative to nonviral vectors. Many viruses efficiently deliver their nucleic acid genomes to mammalian cells as the initial critical step in their life cycle. Therefore, viruses have been perfected throughout millions of years of evolution for the task of gene delivery. A key to exploiting viruses as gene delivery vehicles is to introduce therapeutic genes into their genomes while concurrently removing the native viral genes that code for harmful viral proteins. The recombinant virus then functions purely as a vector that delivers the therapeutic gene to the nucleus of the target cell without causing cellular damage or subsequent virus propagation.

Viral vectors are generated by exploiting the packaging signal sequences that direct viral genomes into viral particles. A packaging signal sequence is a nucleic acid sequence contained within the viral genome that adopts a specific conformation. Typically, the packaging signal sequence is recognized with high specificity by one of the structural proteins that participates in the assembly of the proteinaceous core of the virus. In a virally infected cell, the viral genome is copied and amplified, the viral genes are expressed, and the structural proteins are assembled to form new virus particles that interact with the progeny viral genomes guided by the all-important packing signal sequence to form fully infectious progeny virus particles that are released from the cell. To generate viral vectors, the packaging signal sequence is removed from the viral genome and appended to the therapeutic transgene. This packageable transgene is then introduced into a mammalian cell along with the viral genes, now lacking their packaging signal sequence such that the viral genes are expressed and new viral particles produced, but only the therapeutic transgene is packaged into the particles because it is now the only nucleic acid in the cell that carries the packaging signal sequence.

Virtually any virus can be exploited as a gene delivery vehicle. However, at present, the most widely used viral vectors are derived from the following viruses: retrovirus (and lentivirus), adenovirus, adeno-associated virus (AAV), and herpes simplex virus. Each viral vector has distinct characteristics that may make it more or less suitable for particular gene therapy applications.

Retroviral and lentiviral vectors are derived from C-type retroviruses such as murine leukemia virus or from lentiviruses such as human immunodeficiency virus and feline immunodeficiency virus. The viral particles are roughly spherical, 80 to 110 nm in diameter, comprising an icosahedral protein core that contains two copies of the 7- to 11-kb single-stranded RNA viral genome plus three virally encoded enzymes: reverse transcriptase, protease, and integrase. The core is surrounded by a lipid envelope that carries the viral envelope glycoproteins responsible for virus attachment and entry. After attachment, the virus envelope fuses with the cell membrane, and the core moves toward the nucleus. The viral RNA is reverse transcribed to double-stranded DNA and transported into the nucleus where the integrase directs its insertion into the host chromosomal DNA at a random site. Viral genes are transcribed from the integrated (proviral) DNA. To make retroviral vector particles, two helper plasmids are expressed in a packaging cell, one coding for core proteins and viral enzymes and one for envelope glycoproteins. The packageable RNA that codes for the therapeutic protein is transcribed from a third plasmid, the vector plasmid. Murine leukemia virus-based retroviral vectors do not integrate or express in quiescent cells. Cell division is required for integration. In contrast, lentiviral vectors can integrate in quiescent cells. Integration is semi-random, using a different chromosomal site in each transduced cell with an overall preference for transcriptionally active target sites. Expression of the transgene varies substantially from cell to cell according to the integration site. Random integration is associated with a risk of cell transformation (insertional mutagenesis) caused by disruption of a tumor suppressor gene or activation of a cellular oncogene.

Retroviral and lentiviral vectors have a capacity of 8 kb and provide maximum titers up to $10^{10}$ IU/mL. Because of integration, the transgene persists in the progeny of the originally infected cells. Vector particles are immunogenic, but vector-transduced cells express no viral gene products and are therefore nonimmunogenic. The expression profile peaks within 72 hours and then gradually declines over weeks, months, or years because of transgene methylation, acetylation, provirus deletion, or death of the target cell.

Adenovirus vectors are nonenveloped viruses with an 80- to 110-nm-diameter icosahedral protein shell that contains a 35- to 40-kb doublestranded DNA genome. The fiber proteins appear on electron microscopy as prominent spikes at the twelve vertices of the icosahedron. Primary attachment to the target cell is through the fiber protein, and secondary attachment to cell-surface integrin receptors occurs through the penton base protein that anchors the fiber at the vertices of the icosahedron. After endocytosis, the virus disrupts the wall of the endosome and is released into the cytoplasm. The cytoplasmic virus migrates to the nuclear envelope and delivers the viral DNA to the nucleus. In wild-type adenovirus infection, early (nonstructural) viral genes are expressed initially, and the early proteins drive virus genome replication and late (structural) gene expression. To produce adenovirus vectors, early genes (e.g., E1, E4) are deleted from the virus genome to disrupt the replication cycle, and therapeutic genes are inserted in their place. Vector particles are produced in cell lines that stably express the missing early gene products (e.g., E1, E4) and can therefore support vector replication. In helper-dependent ("gutless") adenovirus vectors, all the viral coding sequences are removed. Production of helper-dependent vectors requires the addition of a replicating helper adenovirus that is later removed from the vector stock.

Adenovirus vectors have a capacity of approximately 8 kb for conventional vectors and 30 kb for helper-dependent vectors, and titers up to $10^{14}$ IU/mL are possible, allowing for high target cell transduction efficiencies. The vector genome persists in the cell as a linear, unintegrated episome and is therefore diluted by cell division. Adenovirus particles are immunogenic as are transduced cells in the setting of conventional adenovirus vectors because of low-level expression of viral structural genes. However, cells transduced with helper-dependent adenovirus vectors express no viral proteins and are not immunogenic. The adenoviral vector expression profile reaches an extremely high peak within the first three days and is then rapidly lost in the setting of conventional vectors because of immune-mediated destruction of transduced cells. However, with helper-dependent vectors, expression is maintained throughout weeks, months, or years because target cells are not subject to immune-mediated destruction.

Adenoassociated virus is an extremely small, nonenveloped icosahedral virus (18 to 26 nm in diameter); carrying a single-stranded DNA genome of approximately 5 kb with short, inverted terminal repeats required for genome replication and packaging. An apathogenic dependovirus, AAV replicates only in cells that are concurrently infected with a suitable helper virus (adenovirus or herpes virus). After virus attachment and translocation across the target cell membrane, the single-stranded DNA genome is transported to the cell nucleus where it is converted to double-stranded DNA, which is then transcribed by cellular polymerase. The AAV genome can persist in the cell nucleus, either as linear, unintegrated DNA or as integrated into the cellular chromosome. To generate AAV vectors, the vector genome, comprising an expression cassette flanked by AAV-inverted terminal repeats, is introduced into mammalian packaging cells along with a plasmid coding for the AAV proteins and a second plasmid coding for necessary adenovirus helper functions.

Having a capacity of 5 kb, AAV vectors can be produced at titers up to $10^{12}$ particles per milliliter. Adeno-associated virus genomes persist in the cell nucleus as episomal or integrated DNA. The particles are immunogenic, but transduced cells express no viral proteins. The transgene expression profile slowly increases during a period of weeks and then persists long-term with gradual decline.

Herpes simplex virus is a fairly complex enveloped virus, 120 to 300 nm in diameter, that carries a double-stranded DNA genome of 152 kb. The icosahedral core, which houses the viral genome, is approximately 100 nm in diameter and is separated from the envelope by the tegument. Herpes simplex virus has a strong tropism for sensory neurons. Three waves of gene expression occur during the viral life cycle. Initially, the immediate early genes are expressed, and this leads to expression of the early genes, which in turn leads to expression of the late genes that generally code for viral structural proteins. Replication-defective herpesvirus vectors are constructed by removing critical immediate early genes such as infected cell protein (ICP)-4 and ICP-27 from the viral genome, which is then grown on complementing cells that stably express ICP-4 and ICP-27. Herpesvirus vectors have a significantly higher capacity for foreign genetic material than the vectors described previously and are rapidly gaining popularity for central and peripheral nervous system applications. Herpes simplex virus is able to enter into a latent state in sensory neurons, and this is one of the major reasons for its popularity as a vector for these cells.

The choice of an appropriate vector system for AGR3 gene therapy protocol should be guided by consideration of the relevant properties of the different vector systems in relationship to the characteristics of the target cell population and the goals of the proposed application. When the targets of therapy are cancer cells and the goal is to eliminate them, the highest priority is for a vector that can transduce the cells with an extremely high efficiency. In this setting, a strong immune/inflammatory response to the genetically modified cells is not contraindicated and may be desirable to increase the potency of the therapy. Therefore, conventional adenovirus vectors are appealing. Results of experiments conducted thus far indicate that expression of AGR3 in normal (i.e., non-cancer) cells has no detectable effect. Thus, a vector with wide tropism might be employed.

There are three broad strategies whereby vectors can be targeted to accumulate at predetermined sites or selectively transduce a particular target cell population, two of which may be employed to deliver an AGR3 polynucleotide. In one approach, regional delivery is used to ensure accumulation of vector at a particular site in the body, e.g., aerosol delivery to airways, a stereotactically guided injection into the brain, or painting vector onto vascular structures during surgical exposure. The second approach is to modify the vector (intrinsic targeting) such that it recognizes and transduces the target cells with high specificity but is incapable of transducing nontargeted cells. For viral vectors, transductional targeting can be achieved by direct chemical modification of the virus coat, by use of bifunctional cross-linking molecules that provide a bridge between the vector and the cell surface target, or by direct engineering of the viral attachment proteins. Transductional targeting is an active area of research, and proof of principle has been established for all major vector systems.

In one method, molecules that target cell surface markers associated with adenocarcinomas (or other AGR2 expression enhanced cancers) may be used. These include antibodies or other biological or small molecules that target, e.g., CD57, CD44, CD24, ESA, ABCG2, TROP2, CA125 or CD4.

In addition or as an alternative to transductional targeting, transcriptional targeting may be employed. The narrowest definition of a gene is that it is a nucleic acid sequence that codes for a specific protein. In general, protein-coding sequences in a mammalian chromosome are divided into several exons separated from each other by long intronic sequences containing donor and acceptor sites for the cellular splicing machinery and are flanked by RNA processing signals that direct addition of a 5' cap and 3' polyadenylation signal and determine RNA stability. Transcriptional or DNA control sequences or elements, including the promoter, enhancers, silencers, and locus control elements, are also essential and integral components of the gene that function as landing pads for nuclear proteins (transcription factors) that regulate the level and timing of gene expression. The transcriptional promoter is located immediately upstream of the first exon. Transcriptional enhancer and silencer elements regulate the activity of the promoter element and may be located upstream or downstream of the gene or in one of the introns in either orientation, often a considerable distance from the promoter element. Locus control elements are typically found at a considerable distance from the coding sequences in a 5' or 3' direction and are the main determinants of chromatin conformation (open or closed) within a genetic locus.

Transcriptional control elements are portable and can be transferred from one gene to another, retaining their tissue specificity. Promoters and enhancers from housekeeping genes expressed in all tissues or from certain viruses (e.g., cytomegalovirus) drive gene expression promiscuously in all transduced mammalian cells. Promoters and enhancers from genes expressed in a tissue-specific manner drive expression of foreign genes with the same tissue specificity. Pharmacological control of gene expression is desirable for certain gene therapy applications. Several drug-regulatable gene expression systems have been developed. For example, the tetracycline responsive system and the lac operator-repressor system (see WO 03/022052 A1; and US 2002/0162126 A1), the ecdyson regulated system, or promoters regulated by glucocorticoids, progestins, estrogen, RU-486, steroids, thyroid hormones, cyclic AMP, cytokines, the calciferol family of regulators, or the metallothionein promoter (regulated by inorganic metals).

In considering typical steps of a biotechnological production process to synthesize an AGR3 therapeutic, production starts with the selection of an appropriate species and strain and the engineering of an expression system that enable high product yields and permit easy handling during strain development, fermentation, and downstream processing. Industrially established expression systems for production of marketed compounds include body-forming *Escherichia coli* strains, the yeast *Saccharomyces cerevisiae* and mammalian cells like CHO- and BHK-cells. Classic measures for improvement of the selected strains and expression systems are mutation and selection runs, breeding, directed genomic alterations, metabolic engineering, and measures aimed at the enhancement of expression rates of genes involved in product biosynthesis. Cultivation of cells occurs under suitable conditions permitting strong growth, high product yield, and high product quality and facilitating product recovery and purification during downstream processing, which usually starts with separation of the product from the biomass and the culture broth by centrifugation or filtration. Before the separation of intracellular-occurring products, cells have to be ruptured by high-pressure homogenization. For high product purity, high recovery rates and simultaneous maintenance of the pharmacological activity, product purification and polishing usually occurs by solvent and solid-phase extraction. The choice of suitable resins and solvents and their combinations is highly dependent on the chemical and physical properties of the product and the side metabolites to be removed. The final step consists of product concentration and drying, e.g., by heat, freezing, and/or vacuum before the galenic preparation. Galenic preparing and filling involve addition of galenic excipients, supplements, stabilizers, and adjuvants.

The AGR3 therapeutic to be used for in vivo administration must be sterile. This is readily accomplished by filtration through sterile filtration membranes, prior to or following lyophilization and reconstitution. The AGR3 therapeutic ordinarily will be stored in lyophilized form or in solution. The AGR3 therapeutic generally is placed into a container having a sterile access port, for example, an intravenous solution bag or vial having a stopper pierceable by a hypodermic injection needle.

The route of administration for the AGR3 therapeutic is in accord with known methods. Examples of parenteral administration include subcutaneous, intramuscular, intravenous, intraarterial, and intraperitoneal administration, or by sustained release systems as noted below. Subcutaneous and intravenous injection or infusion is preferred. Also, as advances in the administration of protein or polynucleotide therapeutics are made, it will be well within the skill on one in the art to adapt such advances to the AGR3 therapeutics in the methods of the invention as described herein.

As a general proposition, the total pharmaceutically effective amount of therapeutic agent administered parenterally per dose will be in the range of about 1 µg/kg/day to 10 mg/kg/day of patient body weight, although, as noted above, this will be subject to a great deal of therapeutic discretion. More preferably, this dose is at least 10 µg/kg/day, and most preferably for humans between about 25-50 µg/kg/day. If given continuously, the therapeutic agent is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. Preferably in human patients, a pharmaceutically effective amount of the therapeutic agent administered parenterally per dose will be in the range of about 10 to 100 micrograms per kilogram of patient body weight per day.

Practitioners devising doses of therapeutic agents should take into account the known side effects and contraindications of the AGR3 therapeutics, if any. As noted above, however, these suggested dosages of AGR3 therapeutics are subject to a great deal of therapeutic discretion. The key factor in selecting an appropriate dose and scheduling is the result obtained, as indicated above.

Since the present invention relates to treatment of cancer with AGR3 therapeutic compounds, the invention also includes kits comprising pharmaceutical compositions for administration to a patient.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

General Methods

Cell Lines.

H460 lung adenocarcinoma cells were grown in DMEM containing 4.5 g/L glucose and L-glutamine, and supplemented with 10% fetal bovine serum, 50 U/ml penicillin, and 50 µg/ml streptomycin. Esophageal adenocarcinoma cell lines JH-EsoAd1 and OE33 were also used in the studies. JH-EsoAd1 cells (Alvarez et al., Cancer Biol Ther, 7:1753-55 (2008)) were cultured in RPMI1640 with 20% FBS, OE33 cells (Boonstra et al., J Natl Cancer Inst, 102:271-74 (2010)) were obtained from Sigma-Aldrich (St. Louis, Mo.) and cultured in RPMI1640 with 10% FBS. NIH3T3 cells were grown at 37° C. in a moist atmosphere with 5% $CO_2$ in DMEM supplemented with 4.5 g/L glucose, 1-glutamine (Cellgro, Mediatech, Inc.), penicillin (100 units/mL), streptomycin (100 ug/mL), and 10% (v/v) fetal bovine serum. Cells infected with retroviral vectors containing shRNAmir constructs were grown in media containing 2 µg/ml puromycin. Cells transfected with full-length cDNA constructs of human AREG, AGR2 or AGR3 used the pcDNA3.1 expression vector (Invitrogen, Life Technologies Corp., Carlsbad, Calif.) and were selected in media containing 0.8 mg/ml G418.

NCBI Reference Sequences.

Human AGR3 (hAGR3): mRNA NM_176813.3; protein NP_789783.1. Human AGR2 (hAGR2): mRNA NM006408.3; protein NP_006399.1. Human Yes-associated protein (hYAP1): mRNA NM_001130145.2 (variant 1), NM_006106.4 (variant 2), NM_001195044.a (variant 3), NM_0011657.2 (variant 4); protein NP_001123617.1 (isoform 1), NP_006097.2 (isoform 2), NP_001181973.1 (isoform 3), NP_001181974.1 (isoform 4). Human amphiregulin (hAREG): mRNA NM_001657.2; protein NP_001648.1.

Antibodies.

Primary antibodies used included AREG (RB-257P, Thermo Fisher Scientific), β-actin (A2066, Sigma-Aldrich Inc., St. Louis, Mo.), AKT (9272, Cell Signaling Technology, Danvers, Mass.), pAKT (4058, Cell Signaling), Erk1/2

(9102, Cell Signaling), pErk1/2 (9106, Cell Signaling), pYAP (4911, Cell Signaling), pEGFR (2236, Cell Signaling), YAP (sc-15407, Santa Cruz Biotechnology, Santa Cruz, Calif.), EGFR (E12020, Transduction Laboratories, Lexington, Ky.), and a neutralization antibody for AREG (AF262, R&D Systems, Minneapolis, Minn.). Rabbit anti-human AGR2 specific polyclonal antisera was generated against a peptide containing the sequence representing amino acids 21-39 of human AGR2 (NP_006399), and showed no cross-reactivity for AGR3.

RNA Interference.

RNA interference was achieved using microRNA-adapted shRNAmir (Silva et al., Nat Genet, 37:1281-88 (2005)). Specific shRNAmir sequences for AGR2 (OpenBiosystems, Irvine, Calif.) were subcloned into the MSCV-LTRmiR30-PIG (LMP) retroviral vector as previously described in Wang et al., Cancer Res, 68:492-97 (2008). RNA interference for YAP1 was achieved using shRNAmir sequences incorporated into pGIPZ Lentiviral vectors (OpenBiosystems, Clone ID V3LHS_306099), which were packaged using the TransLenti Viral GIPZ packaging system. Seventy-two hours after infection with lentivirus shRNAmir specific for YAP1, the cells were harvested and processed by FACS sorting for GFP fluorescence (FACS Vantage cell sorter, BD Biosciences, San Jose, Calif.). FACS sorting was employed because only 30% of cells expressed high GFP, which served as a surrogate marker for shRNAmir expression.

Quantitative PCR.

RNA levels were quantified using real-time PCR. Total RNA was isolated from cells using TRIzol® reagent (Invitrogen). First-strand cDNAs were synthesized from total RNA using Superscript II reverse transcriptase (Invitrogen) with random hexamer primers. Quantitative PCR reactions were performed using the IQ SYBR Green Supermix and the iCycler iQ™ detection system (Bio-Rad Laboratories, Richmond, Calif.).

Protein Immunoblotting.

Protein concentration of cell lysates was determined using a spectrophotometer (NanoDrop 2000, Thermo Fisher Scientific, Wilmington, Del., Inc.). Protein samples were resolved using a 4-12% Bis-Tris gel (Invitrogen) and transferred to PVDF membranes (Millipore Corporation, Bedford, Mass.). Membranes were blocked in 5% non-fat skim milk in TBS-Tween (20 mM Tris, 137 mM NaCl, 0.1% Tween 20, pH7.6) for 1 hour and incubated with primary antibodies. Detection was achieved with the appropriate secondary antibodies and enhanced chemiluminescence (GE Healthcare, Piscataway, N.J.) Immunoblots were quantified using a flatbed scanner (Hewlett-Packard Scanjet, Palo Alto, Calif.) and Adobe Photoshop software (Adobe Systems Inc., San Jose, Calif.).

Assays for Cell Proliferation and Anchorage-Independent Growth.

Cell proliferation was determined by plating $1\times10^4$ cells in a 24-well tissue culture plate in 0.5 ml of DMEM supplemented with 0.5% FBS. The cells were harvested at different time points, mixed with an equal volume of trypan blue, and manually counted using a hemacytometer. Each time point is represented by the mean of three wells. Anchorage-independent growth was assessed by colony formation in soft agar (Wang et al., Cancer Res, 68:492-97 (2008); Cox and Der, Methods Enzymol, 238:277-94 (1994)). Cells were plated in DMEM supplemented with 10% FBS and 0.33% (w/v) Bacto-Agar (Difco, Detroit, Mich.) on top of a 0.6% agar bottom layer. The cells were fed weekly with DMEM supplemented with 10% FBS. After two weeks, the colony number was visually determined with a microscope.

Immunohistochemistry.

Immunohistochemistry was performed using paraffin-embedded formaldehyde fixed tissue sections. Antigen retrieval was enhanced by microwave heating in 10 mM citrate buffer (pH 6.0) for 12 minutes. Endogenous peroxidase was quenched using 1.5% $H_2O_2$, followed by blocking with 5% normal goat serum diluted in PBS. The primary antibodies used were those previously noted and used at 1:200 in blocking serum. Sections were later treated with biotinylated secondary antibody for 30 minutes and ABC reagent for 45 minutes (PK-6101, Vector Labs, Burlingame, Calif.). Visualization was achieved using the horseradish peroxidase substrate (DAKO, Carpinteria, Calif.). Imaging was achieved using a Nikon E600 microscope.

Statistical Analysis.

When indicated, statistical differences were calculated using a nonparametric test (unpaired t test, 2-tailed) for unpaired samples, and differences between groups were compared using ANOVA (GraphPad Software, San Diego, Calif.).

Miscellaneous Methods.

The assays for focus-formation were performed as previously described (Cox and Der, supra (1994). Culture plates containing foci were stained with crystal violet, scanned on a flatbed scanner, and quantified using ImageJ. Secreted AREG was measured using the Amphiregulin Duo-set ELISA kit (DY262, R&D Systems, Minneapolis, Minn.). For the ligand blocking studies, goat anti-human AREG antibody (R&D Systems, Minneapolis, Minn.) was resuspended in PBS at 100 µg/ml and applied to cells serum starved for 48 hours at a concentration of 1 µg/ml antibody. Cells were incubated with the antibodies for 2 hours before lysis for protein immunoblotting.

Example 2

AGR2 and AREG are Co-Expressed in Human Adenocarcinoma Cells

The expression of AGR2 and the EGFR ligand, AREG, has been described in many human adenocarcinomas of similar origin, and previous gene expression studies using DNA microarrays has established that AGR2 is expressed in all esophageal adenocarcinomas and its premalignant precursor, Barrett's esophagus (see Hao, supra (2006)). AGR2 and AREG co-expression in human cancer was explored using immunohistochemistry of surgically-resected esophageal adenocarcinomas. Serial sections of surgically-resected esophageal adenocarcinomas revealed co-expression of AGR2 and AREG proteins by neoplastic cells. Tissue microarrays were then used to determine the prevalence of co-expression for the two genes. All premalignant Barrett's esophagus cases expressed both AGR2 and AREG protein. AGR2 protein was also detected in all cases of esophageal adenocarcinomas, and AREG was similarly detected in 76% of samples (see FIG. 3).

Example 3

AGR2 Expression Induces AREG Expression in Adenocarcinoma Cells

Figure 4A:
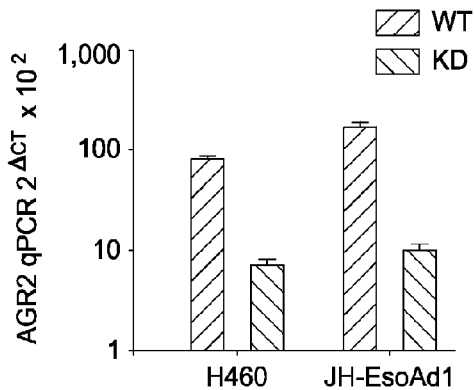
FIGS. 4A through 4F are bar graphs showing results of studies demonstrating that AGR2 induces amphiregulin (AREG) expression in two cell lines.

The relationship between AGR2 and AREG was evaluated using H460 adenocarcinoma cells and JH-EsoAd1 cells, where AGR2 is highly expressed. Immunoblots for AGR2 were performed on cell lysates derived from H460 and JH-EsoAd1 cells after AGR2 knockdown by RNA interference (H460-AGR2KD and JH-EsoAd1-AGR2KD cells). β-actin served as a loading control. "KD" designates knockdown; "WT" designates cells infected with the vector alone. FIG. 4A shows a log plot of AGR2 mRNA qPCR in AGR2WT and KD H460 and JH-EsoAd1 cells. The values are normalized to β-actin mRNA. H460-AGR2WT versus H460-AGR2KD, $p<0.0001$; JH-EsoAd1-AGR2WT versus JH-EsoAd1-AGR2KD, $p=0.0001$. RNA interference-mediated reduction of AGR2 expression thus resulted in an 11.2- and 16.6-fold decrease in mRNA levels and a 9.1- and 3.5-fold decrease in protein expression in H460-AGR2KD and JH-EsoAd1-AGR2KD cells, respectively.

Figure 4B:
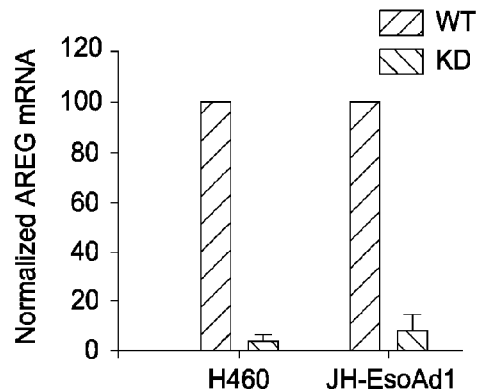

FIG. 4B shows AREG mRNA expression in AGR2 wild type and knockdown cells using real-time quantitative PCR (qPCR) for AREG. Mean qPCR values (n=3) were adjusted such that WT cells equaled 100. H460-AGR2WT versus H460-AGR2KD, $p<0.0001$; JH-EsoAd1-AGR2WT versus JH-EsoAd1-AGR2KD, $p<0.0001$. Results revealed a 27.0- and 12.8-fold decrease in mRNA levels in H460-AGR2KD and JH-EsoAd1-AGR2KD cells, respectively, compared to wild-type controls infected with the empty vector.

Figure 4C:
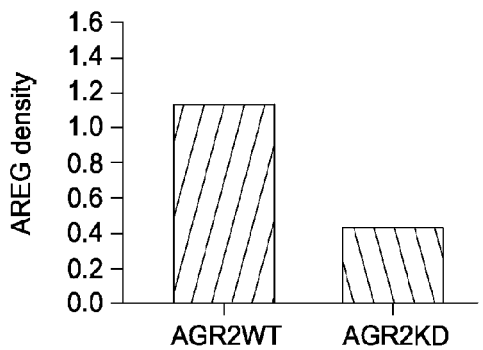
Figure 4D:
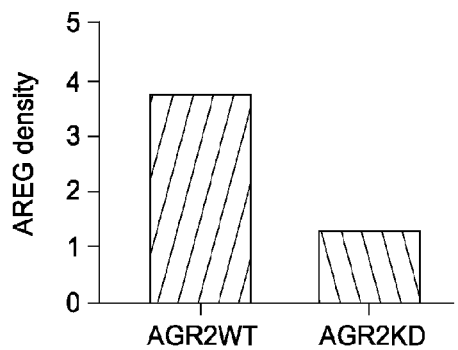

Immunoblots of whole cell lysates for AREG in H460 cells and JH-EsoAd1 cells was performed. The dominant immunoreactive of proAREG is at 50 kDa and the processed form of AREG is at 26 kDa. Scanning densitometry was performed for all AREG immunoreactive bands for H460 (FIG. 4C) and JH-EsoAd1 (FIG. 4D) cells. AREG values were normalized with β-actin. The decrease in AREG mRNA was associated with a 2.6- and 3.0-fold decrease in AREG protein in H460-AGR2KD and JH-EsoAd1-AGR2KD cell lysates, respectively.

Figure 4E:
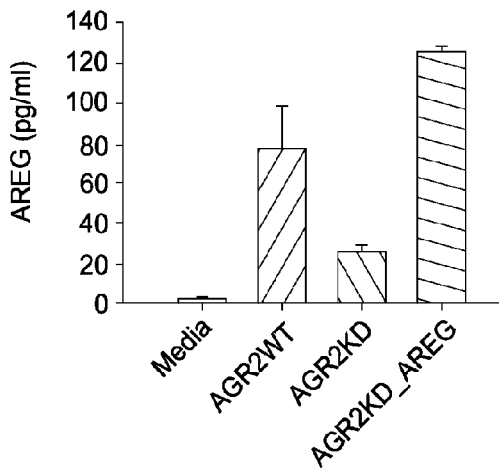
Figure 4F:
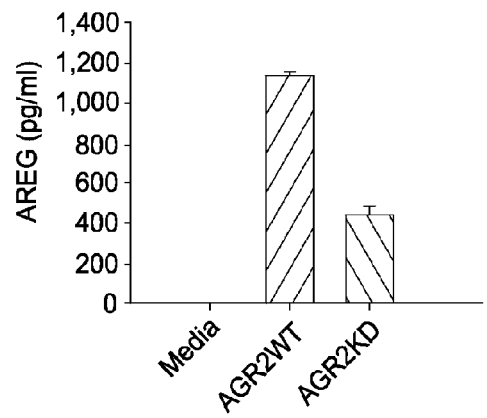

AREG protein is first synthesized as a transmembrane protein that is subsequently released from the plasma membrane by ADAM17 before binding to the EGF receptor. FIGS. 4E and 4F show an ELISA assay for secreted AREG in the culture media for WT and KD H460 (FIG. 4E) ($p<0.0001$) and JH-EsoAd1 cells (FIG. 4F) ($p<0.0001$). Statistical comparisons between the values utilized one-way ANOVA. An ELISA for AREG released into the culture media showed a 3.1 and 2.6-fold decrease in H460-AGR2KD and JH-EsoAd1-AGR2KD cells, respectively. Also shown is the effect of induced AREG expression by transfection (FIG. 4E, column 4). Values represent the mean of three independent experiments. AREG levels in the culture media alone were also assayed as a control (FIGS. 4E and 4F).

Complementary experiments were performed to show that AGR2 overexpression influences AREG expression (results not shown). AGR2 expression in OE33 esophageal adenocarcinoma cells is 29.2-fold lower than H460 cells as determined by qPCR. Transfection of OE33 cells with AGR2 cDNA increased AGR2 mRNA by 42-fold, and resulted in a 7-fold increase in AREG mRNA. Transfection of OE33 cells with AREG cDNA resulted in a 32-fold increase in AREG mRNA, but no significant change in AGR2 expression. Secreted AREG in the culture media from OE33 cells transfected with AGR2 increased by 3.7-fold compared to cells transfected with vector control. Thus AREG expression parallels that of AGR2.

Example 4

AGR2 does not Induce Expression of Other EGF Ligands

The impact of AGR2 expression on other known EGFR ligands and EGFR was also evaluated in H460 and JH-EsoAd1 cells. EGF, TGFα, and HBEGF expression was detected at low levels and was not significantly affected after reducing AGR2 expression. The EGF ligands BTC, EREG, and EPGN were not expressed. Thus only AREG was highly expressed and affected by AGR2 expression. Changes in EGFR mRNA were detected only in H460-AGR2KD cells where a 5.6-fold reduction compared to the wide-type control was observed. AGR2 expression did not affect EGFR expression in JH-EsoAd1 cells. Corresponding results were obtained with AGR2 overexpression in OE33 cells where AREG expression increased, but no significant change in EGF, TGFα, HBEGF, or EGFR expression was observed.

Example 5

AGR2 Expression Stimulates EGF Receptor Signaling

Referring to FIGS. 5A and 5B, the results of immunoblots of total and phosphorylated AKT in H460 (FIG. 5A) and JH-EsoAd1 (FIG. 5B) cell lysates (8 µg) are shown. Cell lysates were derived from wild-type control (WT) and AGR2 knockdown (KD) cells. The quantified relative densities represent the pAKT/total AKT ratio normalized to wild-type cells, which is set at 1.0. Protein immunoblotting of H460-AGR2KD and JH-EsoAd1-AGR2KD cell lysates revealed a 3.5- and 2.3-fold reduction, respectively, in AKT protein phosphorylation after AGR2 expression was reduced with RNA interference.

Example 6

AGR2's effect on the EGFR signaling pathway is mediated by AREG

Whether EGFR signaling induced by AGR2 expression is mediated by AREG was evaluated using an antibody blocking experiment performed in the absence of serum. FIG. 5C shows the pAKT/total AKT ratio as determined by protein immunoblotting of H460 cells as noted. Cells were serum starved for 48 hours followed by treatment with either 1 µg/ml of anti-AREG IgG or control rabbit IgG for 2 hours. The values represent the mean±1SD of 3 independent experiments. Statistical significance between the presence of anti-AREG antibodies and the cell line used (WT, KD, or AREG overexpression) were analyzed by two-way ANOVA ($p=0.0090$). AKT phosphorylation was reduced when AREG mediated signaling was blocked in wild-type H460 or H460-AGR2KD cells with anti-AREG antibodies.

FIG. 5D shows the results of an experiment showing AREG rescue of AGR2 knockdown. The relative densities of immunoblots of total and phosphorylated AKT without (−) and with (+) AREG overexpression by cDNA transfection of H460-AGR2KD (left) and JH-EsoAd1-AGR2KD (right) cells are shown. Although phosphorylated AKT is low in H460-AGR2KD cells, an additional reduction was observed with AREG blocking antibodies. AREG is capable of rescuing the effects of AGR2 knockdown as AKT phosphorylation increased 3.4-fold in H460-AGR2KD cells and 4.0-fold in JH-EsoAd1-AGR2KD cells after transfection with AREG cDNA. The effect, however, is blocked in the presence of AREG blocking antibodies (FIG. 5C, column 6). The absence of AGR2 effects on the other EGF ligands and the results of the antibody blocking experiments indicate that AREG expression represents the major means of EGF pathway stimulation in response to AGR2 expression.

Example 8

AREG Rescues the Transformed Phenotype Associated with AGR2 Knockdown

Figure 6A:
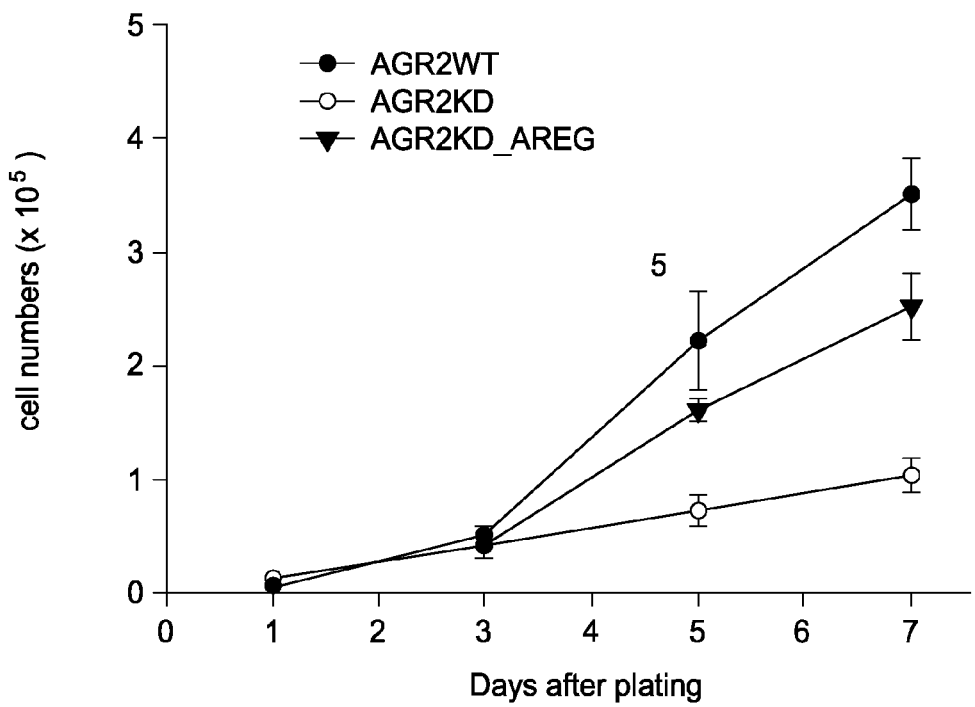
FIGS. 6A and 6B summarize data demonstrating amphiregulin (AREG) mediates the AGR2-induced transformed phenotype.

Previous in vitro work established that AGR2 induces a transformed phenotype based on cell proliferation and anchorage-independent growth (Wang, supra, (2008)), and that transfection of H460-AGR2KD cells with AREG cDNA partially rescued the decrease in cell proliferation. AREG's role in transformation was evaluated by evaluating whether it could rescue the phenotype after AGR2 expression was reduced. FIG. 6A shows a cell proliferation assay of H460 cells AGR2WT, AGR2KD and AGR2KD_AREG that were cultured in 24-well plates ($1\times10^4$ cells/well) in 0.5 ml of DMEM supplemented with 0.5% FBS. The cells were harvested at the specified time points and manually counted. Each data point represents the mean of three wells; error bars=±1 SD. H460-AGR2KD cells grown in 0.5% fetal bovine serum showed a 3.1- and 3.4-fold reduction in proliferation rate 5 and 7 days after initial plating, respectively.

Figure 6B:
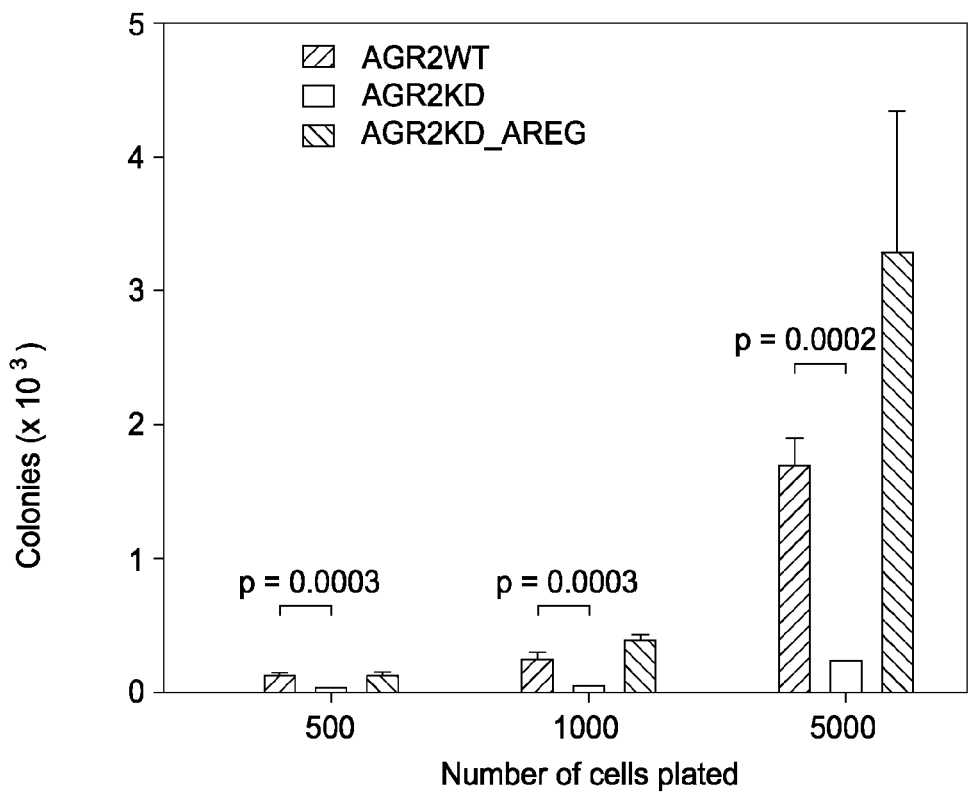

FIG. 6B shows results of an assay of anchorage-independent growth of the same cells as above. Cells were plated in soft agar at different initial densities and assessed for colony number after two weeks. Column height represents the mean colony number from 3 different dishes; error bars=±1 SD. Results show that induced AREG expression in H460-AGR2KD cells also rescued the prior reduction in anchorage-independent growth due to decreased AGR2 expression. These results, along with the results of the antibody-blocking experiments shown in FIG. 5C establish AREG-EGFR signaling as the major signaling pathway mediating AGR2's effects on cell proliferation and anchorage-independent growth in H460 cells. Whether EGFR signaling induced by AGR2 expression is specifically mediated by AREG was evaluated using an antibody blocking experiment performed in the absence of serum.

Example 9

AGR2 Activates the Hippo Pathway Co-Activator, YAP1

A recent study identified the Yes-associated protein (YAP1), a co-activator of transcription in the Hippo pathway, as responsible for AREG expression in a breast epithelial cell line (Zhang et al., Nat Cell Biol, 11:1444-50 (2009)). Whether YAP1 also mediates AGR2-induced AREG expression was evaluated. Immunoblotting with isoform-specific antibodies for phosphorylated and total YAP1 protein in H460 cells was performed. The H460 cells included wild-type controls (WT), AGR2 knockdown (KD), and AGR2—KD_AREG cells where AREG is overexpressed after transfection. The ratio of phosphorylated YAP1 to total YAP1 increased 5.8-fold in H460-AGR2KD cells, and the change in YAP1 phosphorylation was not due to reduced AREG expression because AREG overexpression in H460-AGR2KD cells did not affect YAP1 phosphorylation (results not shown). Thus AGR2 expression results in YAP1 dephosphorylation.

Example 10

YAP1 Activation is Necessary for AGR2 Induction of AREG Expression

Figure 7A:
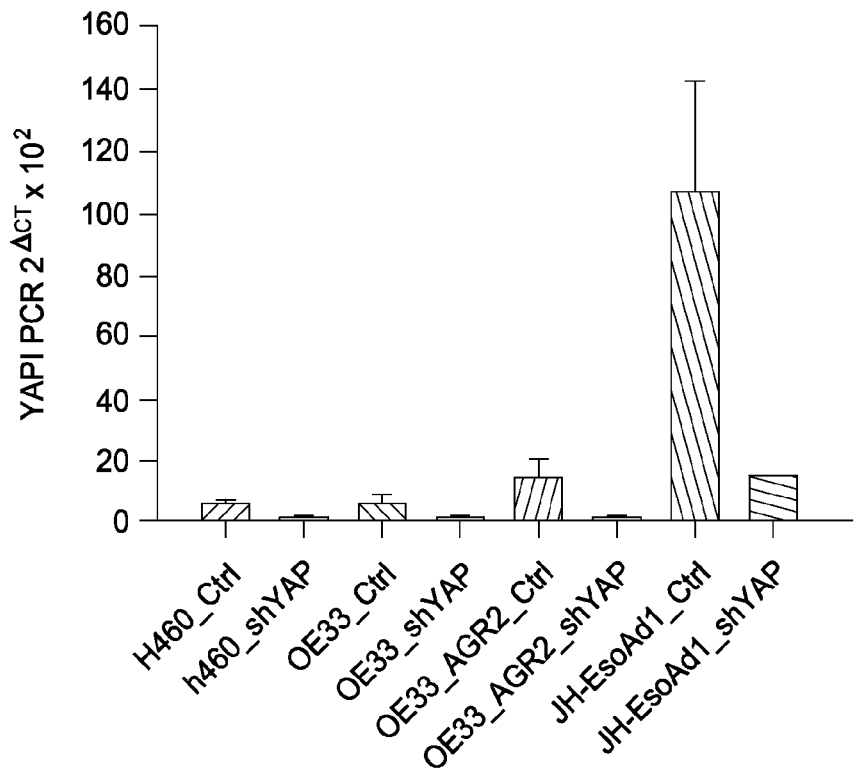
FIGS. 7A through 7C summarize data demonstrating AGR2 induces amphiregulin (AREG) expression through YAP1.
Figure 7B:
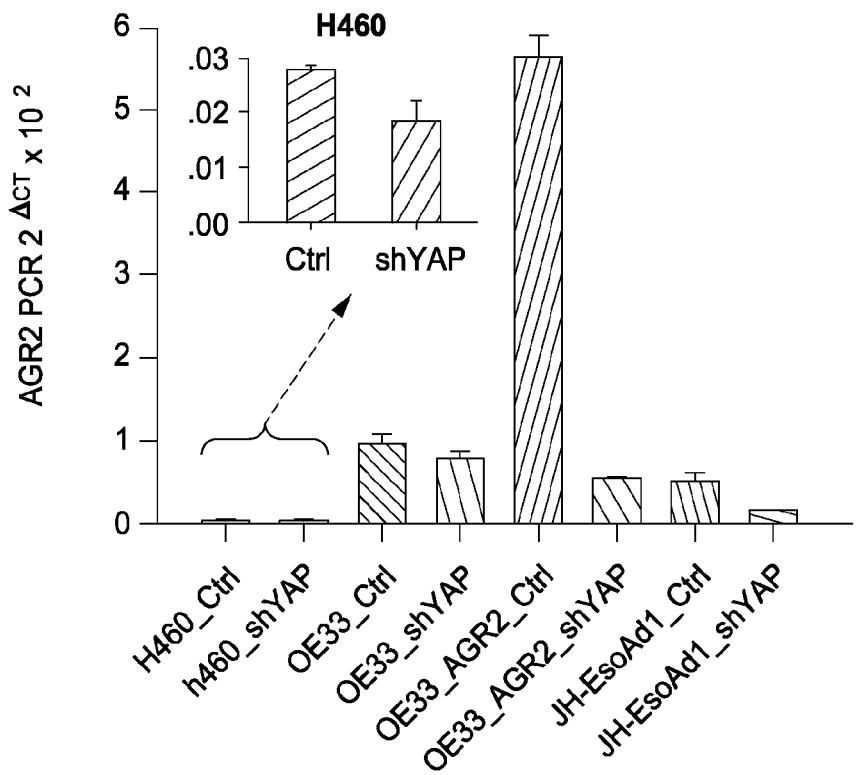
Figure 7C:
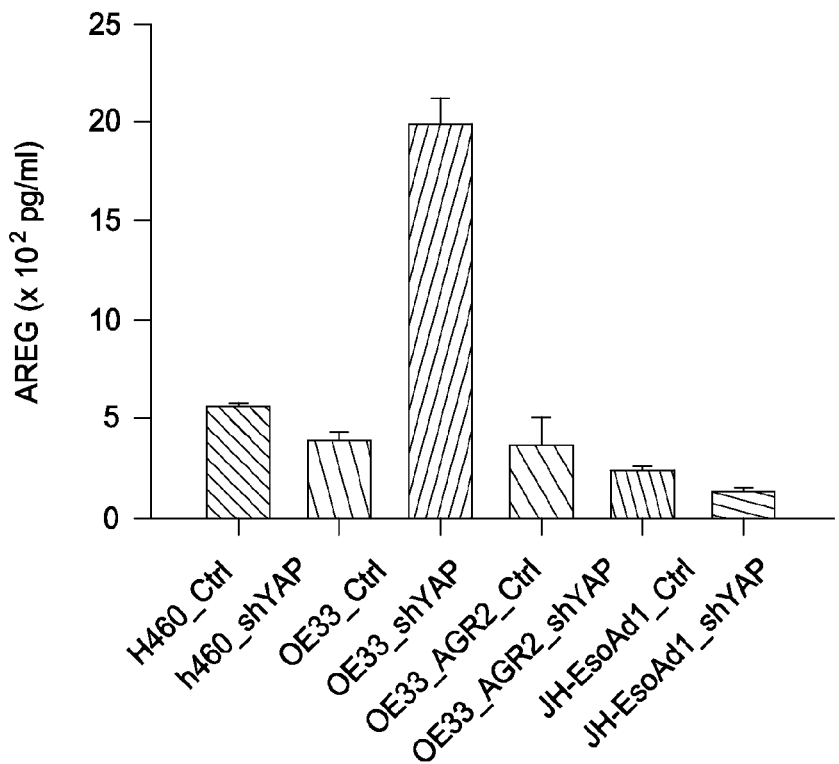

Knockdown of YAP1 expression with RNA interference was performed in H460, OE33, and JH-EsoAd1 cells to evaluate whether reduced YAP1 expression affects AGR2 induced AREG expression. Because decrease YAP1 expression impairs cell growth that precludes drug selection, green fluorescent protein (GFP) was coexpressed with YAP1 RNA interference, which permitted cell sorting of high GFP expressing cells for further analysis. FIG. 7A shows qPCR of YAP1 after expression of YAP1 specific shRNAmir in H460, OE33, and JH-EsoAd1 cells. Before qPCR was performed, the cells were FACS sorted for high GFP expression. OE33-AGR2 represent cells transfected with AGR2 cDNA. Isolated cells from all three cell lines exhibited reduced YAP1 expression (FIG. 7A), which was also associated with lower AREG mRNA levels (FIG. 7B) and secreted AREG protein (FIG. 7C, showing an ELISA for AREG protein in the tissue culture media of OE33 and JH-EsoAd1 cells). AGR2 overexpression in OE33 cells resulted in a 2.2-fold increase in YAP1 mRNA (FIG. 7A, column 5). YAP1 knockdown in OE33 cells that overexpress AGR2 (OE33-AGR2_shYAP) resulted in a 11.2-fold decrease in YAP1 RNA (FIG. 7A, column 6), a 10.6-fold decrease in AREG RNA (FIG. 7B, column 6), and a 5.4-fold decrease in secreted AREG (FIG. 7C, column 4). The loss of AREG expression after YAP1 knockdown was not rescued by AGR2 overexpression (FIG. 7D, column 4). Thus YAP1 is necessary for AGR2 induction of AREG expression.

Example 11

AGR3 as a Negative Regulator of AGR2 Effects

Figure 8:
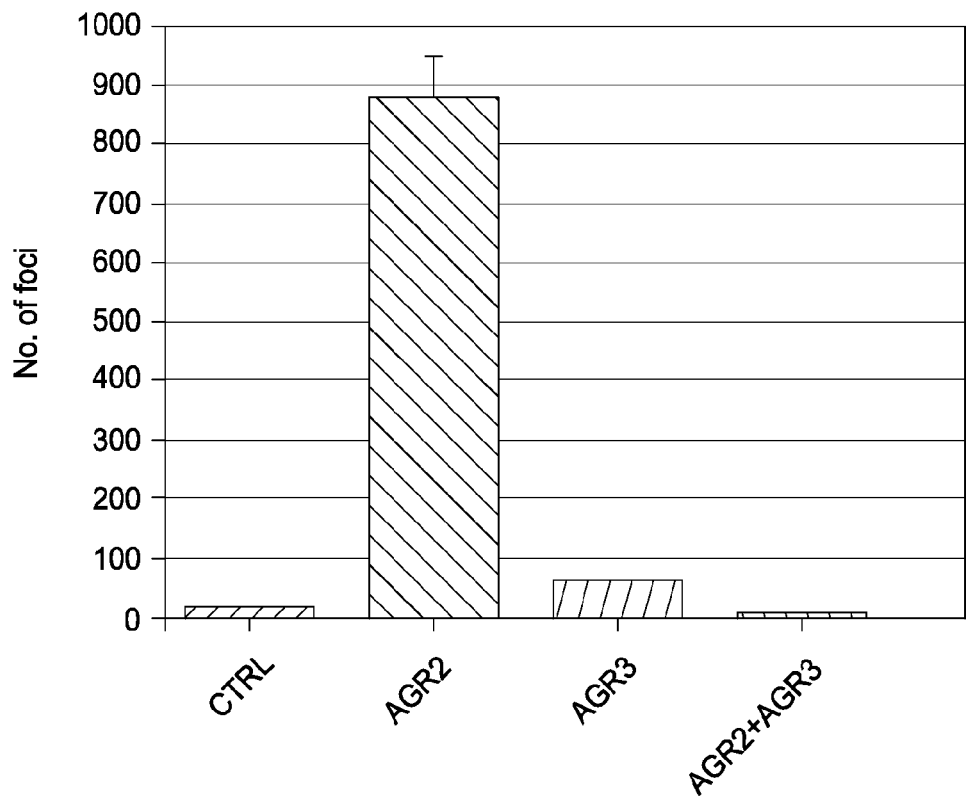
FIG. 8 is a bar graph showing the results of a focus formation assay of NIH3T3 fibroblasts to detect loss of contact-inhibited growth.

AGR3 expression impacts fibroblasts that transgenically express AGR2. Referring to FIG. 8, NIH3T3 fibroblasts were transfected with DNA to express either AGR2, AGR3, or AGR2 plus AGR3. The number of foci reflects the degree of transformation. In NIH3T3 fibroblasts, AGR3 and AGR2 are absent or expressed at low levels. When AGR3 was tested for transforming properties through its expression in NIH3T3 fibroblasts, there was no observable effect, nor did AGR3 induce focus formation as a measure of contact inhibited growth, whereas AGR2 alone was transforming. When AGR2 and AGR3 were co-expressed in NIH3T3 fibroblasts, however, foci formation did not occur. Thus AGR3 is able to abolish AGR2's transforming effects.

Figure 9A:
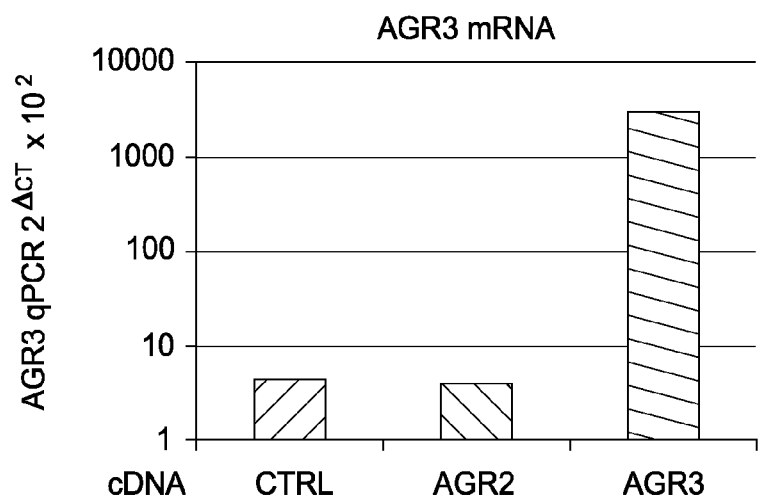
FIGS. 9A through 9C are bar graphs showing expression of AGR3 in H460 lung adenocarcinoma cells results in the marked reduction of AGR2 and AREG expression.
Figure 9B:
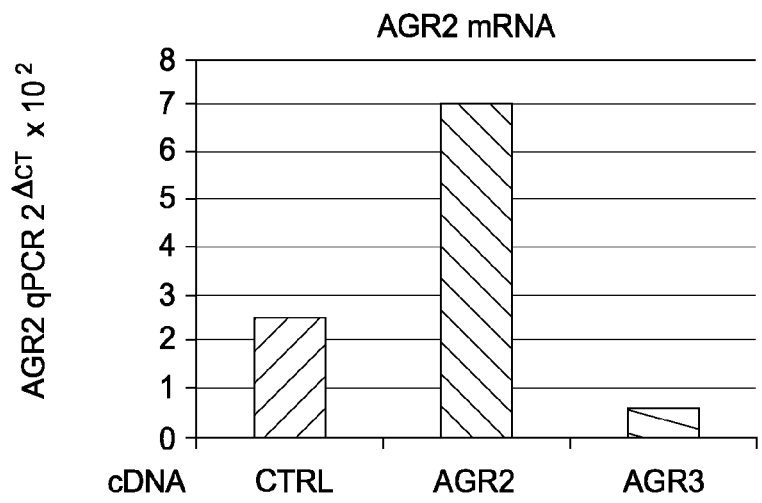
Figure 9C:
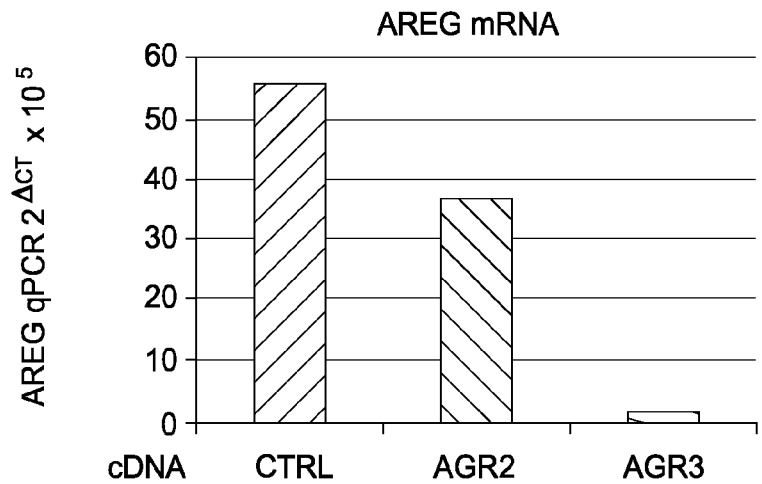

AGR3 expression also impacts adenocarcinoma cell lines that already express AGR2. Referring to FIG. 9, H460 lung adenocarcinoma cells were transfected with control, AGR2, or AGR3 cDNA. mRNA for AGR3, AGR2, and AREG (left to right panels) were then quantified using qPCR. In the H460 lung adenocarcinoma cell line, AGR3 is expressed at low or negligible levels, in contrast to the high AGR2 expression levels. Protein immunoblotting for AGR2 protein of various H460 cells revealed when AGR3 was expressed in H460 lung adenocarcinoma cells, AGR2 mRNA was dramatically reduced (results not shown).

Figure 10:
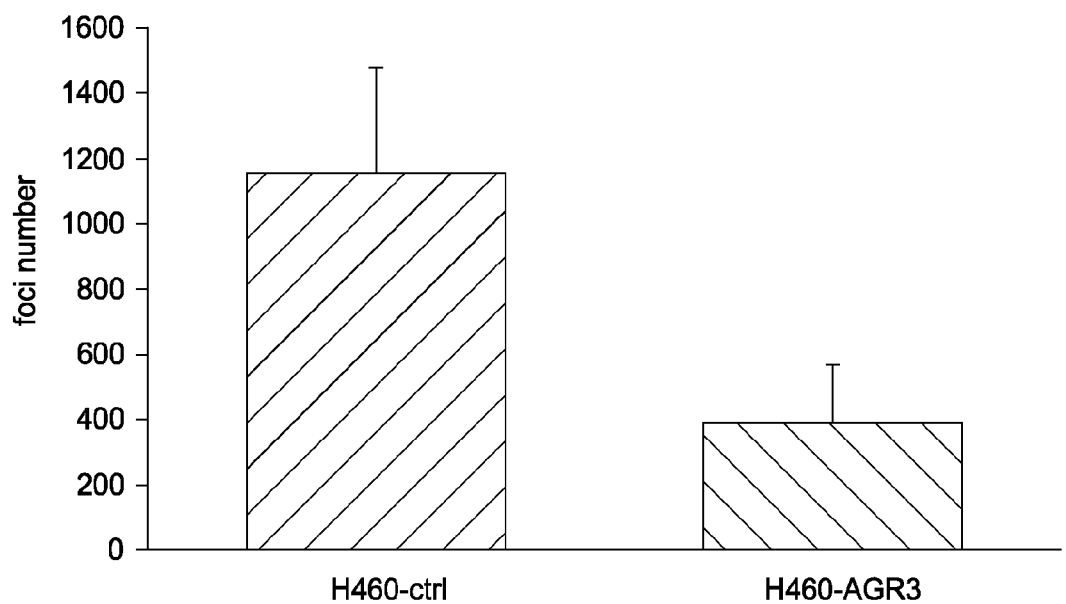
FIG. 10 is a bar graph showing the results of foci formation assays in H460 cells as a measure of contact inhibition.

Along with the reduction in AGR2 mRNA, expression of was also markedly reduced. Referring to FIG. 10, wild-type H460 lung adenocarcinoma cells were compared to H460 cells transfected with AGR3 cDNA. The assay for focus formation was conducted by plating $1\times10^6$ cells/60 mm dish in triplicate for each cell line. The number of foci was counted after 1-2 weeks. The data demonstrate reduction in foci formation with AGR3 expression. Together with the reduction in AGR2 and AREG expression, foci formation by the adenocarcinoma cells was additionally reduced. Thus AGR3 expression reverses the growth promoting effects of AGR2 in adenocarcinoma cells.

Example 12

Introduction of AGR3 in Multiple Lung Adenocarcinoma Cell Lines Results in the Induction of Apoptosis The previous Example demonstrated that induced AGR3 expression in lung adenocarcinoma cell line H460 resulted in decreased expression of AGR2 and the EGF ligand AREG. With induced AGR3 expression, there was a reduction in foci formation. Additional experiments have found that AGR3 expression resulted in a dramatic induction of cell death via apoptosis. Using two different lung adenocarcinoma cell lines, H460 and H727, adenovirus-mediated AGR3 expression resulted in apoptosis and cell death (results not shown). Adenovirus-mediated expression of AGR3 also induced apoptosis in HUH-7 hepatocellular carcinoma cells and HT-29 colon cells. The effects to not appear to be as dramatic as that in lung cancer cells (results not shown).

Example 13

AGR3 Expression is Able to Reduce AREG Expression Independent of AGR2

In order to examine whether the effects of AGR3 are dependent on the presence of AGR2 expression, the myoblast cell line C2C12 was employed. C2C12 is a myoblast cell line that expresses high levels of AREG, but does not express AGR2. Expression of AGR3 in C2C12 cells dramatically reduces AREG expression. Thus, AGR3 may not require the presence of AGR2 to affect cells, having an effect on cells via an AGR2 independent pathway.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. §112, ¶6.

---

We claim:

1. A method for reducing the expression of AGR2 in an adenocarcinoma characterized by enhanced AGR2 expression, comprising
    contacting the adenocarcinoma cells in vitro with a vector comprising an AGR3 coding sequence as set forth in SEQ ID NO:1, operably linked to a promoter, wherein AGR3 is expressed in said adenocarcinoma and reduces expression of AGR2.

2. The method of claim 1, wherein the vector is a plasmid.

3. The method of claim 1, wherein the vector is a viral vector.

4. The method of claim 3, wherein the viral vector is derived from a retrovirus, a lentivirus, an adenovirus, an adeno-associated virus, or a herpes virus.

5. A method for reducing the expression of AGR2 in a lung adenocarcinoma characterized by enhanced AGR2 expression, comprising
    contacting the lung adenocarcinoma cells in vitro with an adenovirus vector comprising an AGR3 coding sequence as set forth in SEQ ID NO:1, operably linked to a promoter, wherein AGR3 is expressed in said lung adenocarcinoma and reduces expression of AGR2.

* * * * *

SEQUENCE LISTING

```
<160> NUMBER OF SEQ ID NOS: 2

<210> SEQ ID NO 1
<211> LENGTH: 175
<212> TYPE: PRT
<213> ORGANISM: Homo sapiens

<400> SEQUENCE: 1

Met Glu Lys Ile Pro Val Ser Ala Phe Leu Leu Leu Val Ala Leu Ser
1               5                   10                  15

Tyr Thr Leu Ala Arg Asp Thr Thr Val Lys Pro Gly Ala Lys Lys Asp
            20                  25                  30

Thr Lys Asp Ser Arg Pro Lys Leu Pro Gln Thr Leu Ser Arg Gly Trp
        35                  40                  45

Gly Asp Gln Leu Ile Trp Thr Gln Thr Tyr Glu Glu Ala Leu Tyr Lys
    50                  55                  60

Ser Lys Thr Ser Asn Lys Pro Leu Met Ile Ile His His Leu Asp Glu
65                  70                  75                  80

Cys Pro His Ser Gln Ala Leu Lys Lys Val Phe Ala Glu Asn Lys Glu
                85                  90                  95

Ile Gln Lys Leu Ala Glu Gln Phe Val Leu Leu Asn Leu Val Tyr Glu
            100                 105                 110

Thr Thr Asp Lys His Leu Ser Pro Asp Gly Gln Tyr Val Pro Arg Ile
        115                 120                 125

Met Phe Val Asp Pro Ser Leu Thr Val Arg Ala Asp Ile Thr Gly Arg
    130                 135                 140

Tyr Ser Asn Arg Leu Tyr Ala Tyr Glu Pro Ala Asp Thr Ala Leu Leu
145                 150                 155                 160

Leu Asp Asn Met Lys Lys Ala Leu Lys Leu Leu Lys Thr Glu Leu
                165                 170                 175
```

```
<210> SEQ ID NO 2
<211> LENGTH: 166
<212> TYPE: PRT
<213> ORGANISM: Homo sapiens

<400> SEQUENCE: 2

Met Met Leu His Ser Ala Leu Gly Leu Cys Leu Leu Leu Val Thr Val
1               5                   10                  15

Ser Ser Asn Leu Ala Ile Ala Ile Lys Lys Glu Lys Arg Pro Pro Gln
            20                  25                  30

Thr Leu Ser Arg Gly Trp Gly Asp Asp Ile Thr Trp Val Gln Thr Tyr
        35                  40                  45

Glu Glu Gly Leu Phe Tyr Ala Gln Lys Ser Lys Lys Pro Leu Met Val
    50                  55                  60

Ile His His Leu Glu Asp Cys Gln Tyr Ser Gln Ala Leu Lys Lys Val
65                  70                  75                  80

Phe Ala Gln Asn Glu Glu Ile Gln Glu Met Ala Gln Asn Lys Phe Ile
                85                  90                  95

Met Leu Asn Leu Met His Glu Thr Thr Asp Lys Asn Leu Ser Pro Asp
            100                 105                 110

Gly Gln Tyr Val Pro Arg Ile Met Phe Val Asp Pro Ser Leu Thr Val
        115                 120                 125

Arg Ala Asp Ile Ala Gly Arg Tyr Ser Asn Arg Leu Tyr Thr Tyr Glu
    130                 135                 140

Pro Arg Asp Leu Pro Leu Leu Ile Glu Asn Met Lys Lys Ala Leu Arg
145                 150                 155                 160

Leu Ile Gln Ser Glu Leu
                165
```